United States Patent [19]
Griss et al.

[11] 3,987,047
[45] Oct. 19, 1976

[54] TETRAHYDRO-AZEPINOQUINOLINES

[75] Inventors: Gerhart Griss; Rudolf Hurnaus; Wolfgang Grell, all of Biberach an der Riss; Robert Sauter, Laupheim; Richard Reichl, Ingelheim am Rhein, all of Germany

[73] Assignee: Boehringer Ingelheim GmbH, Ingelheim am Rhein, Germany

[22] Filed: Nov. 5, 1974

[21] Appl. No.: 520,965

[30] Foreign Application Priority Data
Nov. 16, 1973 Germany............................ 2357253
Sept. 3, 1974 Germany............................ 2442097

[52] U.S. Cl. .................... 260/287 CF; 260/239 B; 260/247.1 E; 260/247.1 L; 260/247.5 H; 260/247.2 R; 260/283.5; 260/283 CN; 260/288 CF; 260/289 C; 424/258
[51] Int. Cl.² .......................................... C07D 471/04
[58] Field of Search ................. 260/288 C, 287 CF

[56] References Cited
OTHER PUBLICATIONS
Yokoo et al., "Bull. Chem. Soc. Japan" vol. 29, p. 631 (1959).
Simson et al., "J. Chem. Soc." (1945), pp. 646–657.

*Primary Examiner*—Nicholas S. Rizzo
*Assistant Examiner*—David E. Wheeler
*Attorney, Agent, or Firm*—Hammond & Littell

[57] ABSTRACT
Compounds of the formula

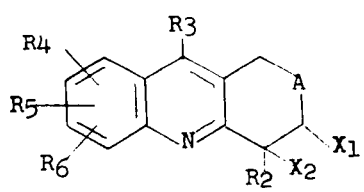

wherein

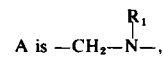

$A$ is $-CH_2-N-$, where
$R_1$ is hydrogen, straight or branched aliphatic acyl of 1 to 12 carbon atoms, methoxy-substituted straight or branched aliphatic acyl of 1 to 12 carbon atoms, benzoyl, halo-benzoyl, carbalkoxy of 2 to 7 carbon atoms, carbcycloalkoxy of 4 to 7 carbon atoms, benzyl, methylbenzyl, phenylsulfonyl, halo-phenylsulfonyl, tolylsulfonyl, alkenyl of 2 to 6 carbon atoms, phenyl, trifluoroacetyl, amidino, amido, thioamido, phenoxycarbonyl, benzyloxycarbonyl, methylsulfonyl or $$-B-X$$

where
$B$ is straight or branched alkylene of 1 to 6 carbon atoms, and
$X$ is hydrogen, hydroxyl, methoxy, carboxyl, cyano, dimethylaminocarbonyl, morpholino-carbonyl or carbalkoxy of 2 to 6 carbon atoms,
$R_2$ is hydrogen, hydroxyl, alkyl of 1 to 3 carbon atoms, alkoxy of 1 to 3 carbon atoms, alkanoyloxy of 1 to 3 carbon atoms, alkoxycarbonyloxy of 2 to 4 carbon atoms, amino, dimethylamino, morpholino or halogen,
$R_3$ is hydrogen, halogen, hydroxyl, carboxyl, straight or branched alkyl of 1 to 6 carbon atoms, cycloalkyl of 3 to 6 carbon atoms, alkoxy of 1 to 3 carbon atoms, phenyl-alkoxy of 1 to 3 carbon atoms, carbalkoxy of 2 to 4 carbon atoms — alkoxy of 1 to 3 carbon atoms, carbalkoxy of 2 to 4 carbon atoms, hydroxymethyl, phenyl, phenoxy, amino, pyrrolidino or morpholino,
$R_4$, $R_5$ and $R_6$, which may be identical to or different from each other, are each hydrogen, halogen, methyl, hydroxyl, methoxy, cyano, amino, nitro, trifluoromethyl, carboxyl, acetyl or carbalkoxy of 2 to 4 carbon atoms, or any two of $R_4$, $R_5$ and $R_6$ together are methylenedioxy, and
$X_1$ and $X_2$ are hydrogen or together form a double bond,
6-N-oxides thereof, and non-toxic, pharmacologically acceptable acid addition salts thereof; the compounds as well as their salts are useful as anoretics.

9 Claims, No Drawings

TETRAHYDRO-AZEPINOQUINOLINES

This invention relates to novel tetrahydroazepinoquinolines, 6-N-oxides thereof and salts thereof, as well as to methods of preparing these compounds.

More particularly, the present invention relates to a novel class of tricyclic aromatic heterocyclic compounds represented by the formula

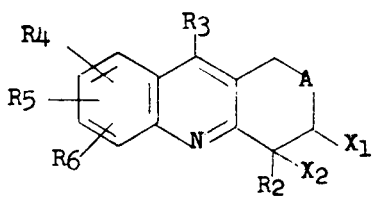

wherein
A is

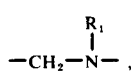

where
$R_1$ is hydrogen, straight or branched aliphatic acyl of 1 to 12 carbon atoms, methoxy-substituted straight or branched aliphatic acyl of 1 to 12 carbon atoms, benzoyl, halo-benzoyl, carbalkoxy of 2 to 7 carbon atoms, carbcycloalkoxy of 4 to 7 carbon atoms, benzyl, methyl-benzyl, phenylsulfonyl, halophenylsulfonyl, tolylsulfonyl, alkenyl of 2 to 6 carbon atoms, phenyl, trifluoroacetyl, amidino, amido, thioamido, phenoxycarbonyl, benzyloxycarbonyl, methylsulfonyl or $$- B - X$$

where
B is straight or branched alkylene of 1 to 6 carbon atoms, and
X is hydrogen, hydroxyl, methoxy, carboxyl, cyano, dimethylamino-carbonyl, morpholino-carbonyl or carbalkoxy of 2 to 6 carbon atoms,
$R_2$ is hydrogen, hydroxyl, alkyl of 1 to 3 carbon atoms, alkoxy of 1 to 3 carbon atoms, alkanoyloxy of 1 to 3 carbon atoms, alkoxycarbonyloxy of 2 to 4 carbon atoms, amino, dimethylamino, morpholino or halogen,
$R_3$ is hydrogen, halogen, hydroxyl, carboxyl, straight or branched alkyl of 1 to 6 carbon atoms, cycloalkyl of 3 to 6 carbon atoms, alkoxy of 1 to 3 carbon atoms, phenyl-alkoxy of 1 to 3 carbon atoms, carbalkoxy of 2 to 4 carbon atoms - alkoxy of 1 to 3 carbon atoms, carbalkoxy of 2 to 4 carbon atoms, hydroxymethyl, phenyl, phenoxy, amino, pyrrolidino or morpholino,
$R_4$, $R_5$ and $R_6$, which may be identical or or different from each other, are each hydrogen, halogen, methyl, hydroxyl, methoxy, cyano, amino, nitro, trifluoromethyl, carboxyl, acetyl or carbalkoxy of 2 to 4 carbon atoms, or any two of $R_4$, $R_5$ and $R_6$ together are methylenedioxy, and
$X_1$ and $X_2$ are hydrogen or together form a double bond,
6-N-oxides thereof, and non-toxic, pharmacologically acceptable acid addition salts thereof.

The compounds of the formula I above and their 6-N-oxides may be prepared by the following methods:

Method A

For the preparation of a compound of the formula I wherein $R_2$ is hydrogen or alkyl of 1 to 3 carbon atoms, by reacting an azepine of the formula

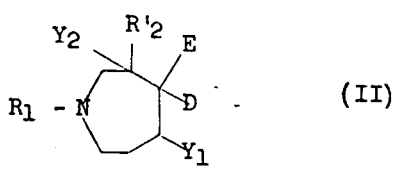

wherein
$R_1$ has the same meanings as in formula I,
$R'_2$ is hydrogen or alkyl of 1 to 3 carbon atoms,
E and D are each alkoxy of 1 to 4 carbon atoms,
$Y_1$ is hydrogen or, together with D, forms a double bond,
$Y_2$ is hydrogen or, together with D, forms a double bond, or
E and D together are oxygen,
with an aniline derivative of the formula

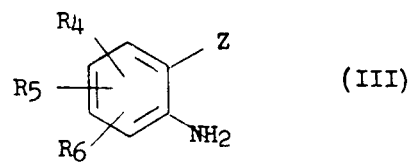

wherein
$R_4$, $R_5$ and $R_6$ have the same meanings as in formula I, and
Z is cyano or $R_3'$— CO —,
where
$R_3'$ is mono- or di-substituted amino or has the meanings defined for $R_3$ in formula I,
under dehydrating conditions, optionally followed by separation of the mixture of isomers thus obtained into its isomeric components.

The reaction is performed with the reactants in the molten state or in the presence of a solvent medium, such as water, benzene or toluene, and advantageously in the presence of a dehydrating agent, such as sodium hydroxide, hydrochloric acid, sulfuric acid, phosphoric acid, phosphorus oxychloride, polyphosphoric acid or p-toluenesulfonic acid, at a temperature between 0° and 200° C. The dehydrating agent may, however, simultaneously serve as the solvent medium. Alternatively, the water formed by the reaction may be continuously removed from the reaction mixture by azeotropic distillation.

When $R_1$ in formula II is inorganic or organic acyl, the reaction is preferably performed in the presence of an acid condensation agent and in a non-aqueous solvent medium.

When $R_3'$ in formula III is hydroxyl and the reaction is performed in the presence of a phosphorus oxyhalide, a mixture of isomers of the formula I wherein $R_3$ is halogen is obtained; and when the reaction is carried out in the presence of polyphosphoric acid, a mixture of isomers of the formula I wherein $R_3$ is hydroxyl is obtained.

The mixture of isomers formed under those conditions, which consists of the compounds of the formulas

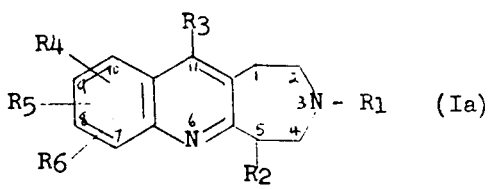

(Ia)

and

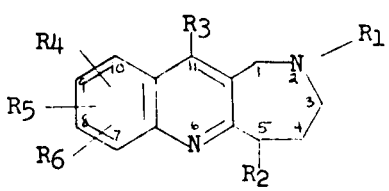

(Ib)

wherein $R_1$ through $R_6$ have the meanings defined above, may subsequently, if desired, be separated into its isomeric components by column chromatography of the bases; or by extraction of the bases or salts, such as the monohydrochlorides or dihydrochlorides; or by fractional crystallization of the bases or salts.

Method B

For the preparation of a compound of the formula I wherein $R_2$ is hydroxyl, acyloxy or alkoxycarbonyloxy, by rearrangement of a compound of the formula

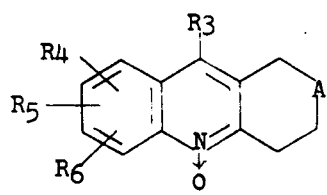

(IV)

wherein $R_3$, $R_4$, $R_5$, $R_6$ and A have the same meanings as in formula I, in the presence of a reactive derivative of an acid, optionally followed by removal of the acyl or carbonic acid ester substituent.

The rearrangement reaction is optionally performed in a solvent medium, such as benzene, dioxane or tetrahydrofuran, in the presence of a reactive derivative of an acid, such as acetic acid anhydride, acetyl chloride, propionic acid anhydride or ethyl chloroformate, and optionally in the presence of a base, such as pyridine or triethylamine, at a temperature between 0 and 100° C. The reaction may, however, also be performed without a solvent medium. The subsequent removal of an acyl or carbonic acid ester substituent is advantageously effected by hydrolysis in the presence of a base or an acid.

If method A or B yields a compound of the formula I wherein one of substituents $R_1$ through $R_6$ is acyl, chlorine, bromine, methoxy, methylenedioxy, phenoxy, cyano and/or carbalkoxy, that compound may be converted by hydrolysis or ether cleavage into the corresponding compound of the formula I wherein at least one of substituents $R_1$ through $R_6$ is hydrogen, hydroxyl and/or carboxyl.

If a compound of the formula I wherein $R_3$ is carboxyl is obtained, it may be converted by means of a chloroformate into a mixed anhydride.

If a compound of the formula I wherein $R_1$ is aralkyl is obtained, it may be converted by catalytic hydrogenation into the corresponding compound of the formula I wherein $R_1$ is hydrogen.

If a compound of the formula I is obtained wherein at least one of substituents $R_1$ through $R_6$ comprises a reactive hydrogen, that compound can be alkylated, acylated and/or vinylated pursuant to known methods.

If method A or B yields a compound of the formula I wherein $R_1$ is alkyl or aralkyl, it may be converted by reaction with a chloroformate into a compound of the formula I wherein $R_1$ is alkoxycarbonyl, cycloalkoxycarbonyl or phenoxycarbonyl.

If a compound of the formula I is obtained wherein $R_1$ is acyl and/or $R_3$ is carboxyl, it can be converted by reduction, such as with lithium aluminum hydride, into the corresponding compound of the formula I wherein $R_1$ is alkyl and/or $R_3$ is hydroxymethyl.

If the reaction product is a compound of the formula I wherein $R_4$, $R_5$ and/or $R_6$ is hydrogen, that compound can be halogenated or nitrated by conventional methods, and the mixture of isomeric nitro-compounds may subsequently be separated into its isomer components.

If a compound of the formula I wherein $R_4$, $R_5$ and/or $R_6$ is nitro, it may be converted by reduction into the corresponding amino-substituted compound which, in turn, may be converted by way of its diazonium salt into a compound of the formula I wherein $R_4$, $R_5$ and/or $R_6$ is halogen, cyano or hydroxyl.

If a compound of the formula I wherein $R_4$, $R_5$ and/or $R_6$ is cyano is obtained, that compound can be converted with a Grignard-reagent and subsequent hydrolysis into the corresponding carbonyl-substituted compound.

If the end product of method A or B is a compound of the formula I wherein at least one of substituents $R_2$ through $R_6$ is hydroxyl, that compound can be converted by conventional methods into the corresponding halo-substituted compound which, in turn, may be converted in conventional manner into the corresponding amino- or alkoxy-substituted compound or the corresponding 3,4- or 4,5-unsaturated compound.

If a compound of the formula I wherein $R_1$ is inorganic or organic acyl or carbalkoxy is obtained, it can be converted by means of an oxidizing agent, such as hydrogen peroxide or perbenzoic acid, into the corresponding 6-N-oxide, and if $R_2$ in such a 6-N-oxide is other than hydrogen and $R_3$ is methyl, that compound can be converted into the corresponding compound of the formula I wherein $R_3$ is hydroxymethyl.

The acylation of a compound of the formula I in which at least one of the substituents $R_1$ through $R_6$ contains a reactive hydrogen is advantageously effected with a reactive derivative of an acid, such as an acid anhydride or halide, or with the corresponding free acid, in the presence of a dehydrating agent, such as thionyl chloride or N,N'-dicyclohexyl-carbodiimide, preferably in a solvent medium, such as water, ethanol, benzene, dioxane, chloroform or dimethylformamide, and optionally in the presence of a base, such as triethylamine, pyridine or sodium carbonate, at a temperature between 0° and 100° C.

The reaction of a compound of the formula I wherein $R_1$ is alkyl or aralkyl with a chloroformate is advantageously performed in a solvent medium, such as methylene chloride, chloroform, ethylene chloride or tetrachloroethylene, at temperatures between 0 and 120°C.

The reduction of a compound of the formula I wherein $R_1$ is acyl and/or $R_3$ is carboxyl is preferably effected with a complex metal hydride, such as lithium aluminum hydride, in a solvent medium, such as ether, ether/dioxane or tetrahydrofuran, at a temperature between 0° and 70° C., but preferably at the boiling point of the particular solvent which is used.

Finally, the conversion of a 6-N-oxide of the formula I wherein $R_2$ is other than hydrogen and $R_3$ is methyl into a corresponding compound in which $R_3$ is hydroxymethyl, is advantageously performed in a solvent medium, such as benzene, dioxane or tetrahydrofuran, in the presence of a reactive derivative of an acid, such as acetic acid anhydride, acetyl chloride, propionic acid anhydride or a chloroformate, at a temperature between 0° and 100° C. The reaction may, however, also be performed without a solvent. The acyl group of the acyloxy-substituted compounds obtained thereby may, if desired, be removed by hydrolysis in the presence of a base or an acid.

The compounds embraced by formula I are organic bases and therefore form acid addition salts with inorganic or organic acids. Examples of non-toxic, pharmacologically acceptable acid addition salts are those formed with hydrochloric acid, sulfuric acid, phosphoric acid, lactic acid, citric acid, tartaric acid, maleic acid, 8-chlorotheophylline or the like.

Most of the starting compounds of the formula II are described in the literature [A. K. Yokoo et al, Bull. Chem. Soc. Japan 29, 631 (1959)]; however, those which are not specifically described may be obtained by means of the Dieckmann-Condensation (Organic Reactions 15, 1-203) from N-substituted 4-[(β-ethoxycarbonyl-ethyl) -amino]-butyric acid ethyl esters, preferably using potassium tert.butylate as the condensation agent, and subsequent hydrolysis and decarboxylation of the intermediate 1-substituted hexahydro-4H-azepinone-(4)-3- and -5-carboxylic ethyl ester isomer mixture in the presence of an acid. The N-acyl-hexahydroazepinone-(4) derivatives are obtained by acylation of hexahydroazepinone-(4).

A 4-alkoxy-azepine of the formula II is obtained by reacting a correspondingly substituted azepinone-(4) with an alkyl orthoformate, and subsequently splitting off alkanol from the intermediate 4,4-dialkoxy-azepine of the formula II (see Belgian Pat. No. 771,330).

The starting compounds of the formula III are either described in the literature (see, for example, J. C. E. Simson et al, J. Chem. Soc. 1945, 646–657) or may be prepared by analogous methods.

The starting compounds of the formula IV may be obtained by oxidizing a corresponding quinoline derivative wherein $R_1$ is acyl with hydrogen peroxide, for example; or by alkylating or acylating a corresponding N-oxide wherein $R_1$ is hydrogen which, in turn, may be obtained by hydrolizing a corresponding acyl-N-oxide.

The following examples illustrate the present invention and will enable other skilled in the art to understand it more completely. It should be understood, however, that the invention is not limited solely to the particular examples given below.

EXAMPLE 1

1,2,4,5-Tetrahydro-11-methyl-3H-azepino[4,5-b]quinoline;

2,3,4,5-tetrahydro-11-methyl-1H-azepino[4,3-b]quinoline; and their dihydrochlorides by method A A mixture consisting of 222 gm (1.48 mol) of hexahydroazepinone-(4) hydrochloride, 200 gm (1.48 mol) of 2-amino-acetophenone and 2.8 liters of 2N hydrochloric acid was heated at the boiling point for 72 hours and was then allowed to cool. The cool reaction solution was made alkaline with sodium hydroxide and then extracted with chloroform. The chloroform extract solution was dried over sodium sulfate, and the chloroform was distilled off, leaving 312 gm (100% of theory) of a mixture of the [4,5-b]and [4,3-b]-isomers in a weight ratio of 4:6.

The isomer mixture thus obtained was dissolved in methanol and chromatographed on a silicagel column (diameter: 10 cm; height: 160 cm; grain size: 0.05–0.2 mm) with methanol as the flow agent. The progress of the column-chromatography was monitored by thin-layer chromatography. Those which contained only one of the respective isomers were combined, and the solvent was distilled out of each combined solution, yielding 95 gm (30% of theory) of the [4,5-b]-isomer of the formula

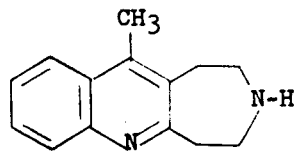

which had a melting point of 103° C., and 104 gm (33% theory of the [4,3-b]-isomer of the formula

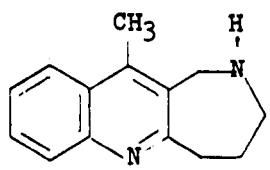

which had a melting point of 123° C.

Each of the isomeric bases thus obtained was separately dissolved in hot isopropanol, the solutions were acidified with isopropanolic hydrochloric acid, and upon cooling the respective dihydrochlorides crystallized out.

Yield of the dihydrochloride of the [4,5-b]-isomer: 90% of theory; m.p. 296° C. (decomp.).

Yield of the dihydrochloride of the [4,3-b]-isomer: 96% of theory; m.p. 284° C. (decomp.).

EXAMPLE 2

1,2,4,5,-tetrahydro-3H-azepino[4,5-b]quinoline, 2,3,4,5-tetrahydro-1H-azepine[4,3-b]quinoline and their dihydrochlorides were prepared from hexahydroazepinone-(4) hydrochloride and 2-amino-benzaldehyde analogous to Example 1.

Yield of the dihydrochloride of the [4,5-b]-isomer: 10% of theory; m.p. 249° C. (decomp.).

Yield of the dihydrochloride of the [4,3-b]-isomer: 24% of theory; m.p. 270° C. (decomp.).

EXAMPLE 3

11-Ethyl-1,2,4,5-tetrahydro-3H-azepino[4,5-b]quinoline, 11-ethyl-2,3,4,5-tetrahydro-1H-azepino[4,3-b]quinoline and their dihydrochlorides were prepared from hexahydroazepinone-(4) hydrochloride and 2-amino-propiophenone analogous to Example 1.

Yield of the dihydrochloride of the [4,5-b]-isomer: 22% of theory; m.p. 270° C. (decomp.).

Yield of the dihydrochloride of the [4,3-b]-isomer: 28% of theory; m.p. 252° C. (decomp.).

EXAMPLE 4

1,2,4,5-Tetrahydro-11-propyl-3H-azepino[4,5-b]quinoline, 2,3,4,5-tetrahydro-11-propyl-1H-azepino[4,3-b]quinoline and their dihydrochlorides were prepared from hexahydroazepinone-(4) hydrochloride and 2-amino-butyrophenone analogous to Example 1.

Yield of the dihydrochloride of the [4,5-b]-isomer: 19% of theory; m.p. 264° C. (decomp.).

Yield of the dihydrochloride of the [4,3-b]-isomer: 19% of theory; m.p. 282° C. (decomp.).

EXAMPLE 5

1,2,4,5-Tetrahydro-11-isopropyl-3H-azepino[4,5-b]quinoline, 2,3,4,5-tetrahydro-11-isopropyl-1H-azepino[4,3-b]quinoline and their dihydrochlorides were prepared from hexahydroazepinone-(4) hydrochloride and 2-amino-isobutyrophenone analogous to Example 1.

Yield of the dihydrochloride of the [4,5-b]isomer: 15% of theory; m.p. 265° C. (decomp.).

Yield of the dihydrochloride of the [4,3-b]isomer: 18% of theory; m.p. 270° C. (decomp.).

EXAMPLE 6

DL-11-sec.Butyl-1,2,4,5-tetrahydro-3H-azepino[4,5-b]quinoline, DL-11-sec.butyl-2,3,4,5-tetrahydro-1H-azepino[4,3-b]quinoline and their dihydrochlorides were prepared from hexahydro-azepinone-(4) hydrochloride and 2-amino-phenyl sec.butyl ketone analogous to Example 1.

Yield of the dihydrochloride of the [4,5-b]-isomer: 12% of theory; m.p. 280° C. (decomp.).

Yield of the dihydrochloride of the [4,3-b]-isomer: 15% of theory; m.p. 255° C. (decomp.).

EXAMPLE 7

1,2,4,5-Tetrahydro-11-isobutyl-3H-azepino[4,5-b]quinoline, 2,3,4,5-tetrahydro-11-isobutyl-1H-azepino[4,3-b]quinoline and their dihydrochlorides were prepared from hexahydroazepinone-(4) hydrochloride and 2-amino-phenyl isobutyl ketone analogous to Example 1.

Yield of the dihydrochloride of the [4,5-b]-isomer: 8% of theory; m.p. 264° C. (decomp.).

Yield of the dihydrochloride of the [4,3-b]-isomer: 13% of theory; m.p. 298° C. (decomp.).

EXAMPLE 8

11-Cyclohexyl-1,2,4,5-tetrahydro-3H-azepino[4,5-b]quinoline, 11-cyclohexyl-2,3,4,5-tetrahydro-1H-azepino[4,3-b]quinoline and their dihydrochlorides were prepared from hexahydroazepinone-(4) hydrochloride and 2-amino-phenyl cyclohexyl ketone analogous to Example 1.

Yield of the dihydrochloride of the [4,5-b]-isomer: 6% of theory; m.p. 225° C. (decomp.).

Yield of the dihydrochloride of the [4,3-b]-isomer: 9% of theory; m.p. 286° C. (decomp.).

EXAMPLE 9

1,2,4,5-Tetrahydro-11-phenyl-3H-azepino[4,5-b]quinoline, 2,3,4,5-tetrahydro-11-phenyl-1H-azepino[4,3-b]quinoline and their dihydrochlorides were prepared from hexahydroazepinone-(4) hydrochloride and 2-amino-phenyl phenyl ketone analogous to Example 1.

Yield of the dihydrochloride of the [4,5-b]-isomer: 31% of theory; m.p. 276° C. (decomp.).

Yield of the dihydrochloride of the [4,3-b]-isomer: 31% of theory; m.p. 335° C. (decomp.).

EXAMPLE 10

1,2,4,5-Tetrahydro-3H-11-azepino[4,5-b]quinolinecarboxylic acid and 2,3,4,5-tetrahydro-1H-11-azepino[4,3-b]quinolinecarboxylic acid by method A A mixture consisting of 5 gm (33.5 millimols) of hexahydroazepinone-(4) hydrochloride, 4.9 gm (33.5 millimols) of isatin, 27 ml of 10 N sodium hydroxide and 27 ml of ethanol was heated at its boiling point for 16 hours. The cooled reaction mixture was neutralized with hydrochloric acid, evaporated to dryness, and the residual isomeric mixture was extracted with hot ethanol (separation of sodium chloride). The chromatographic separation of the isomers was carried out on a silicagel column with methanol as the eluant, as described in Example 1.

Yield of the [4,5-b]-isomer: 6% of theory; m.p. 233° C. (decomp.).

Yield of the [4,3-b]-isomer: 10% of theory; m.p. 269° C. (decomp.).

EXAMPLE 11

11-Chloro-2,3,4,5-tetrahydro-1H-azepino[4,3-b]quinoline was prepared by heating a mixture of 48 gm (0.35 mol) of anthranilic acid, 52.4 gm (0.35 mol) of hexahydroazepinone-(4) hydrochloride and an excess of phosphorus oxychloride. After cooling, ice water was added, and the mixture was extracted with chloroform. The crude product was purified by column chromatography on silicagel with methanol as the eluant.

Yield: 4% of theory; m.p. 127° C.

EXAMPLE 12

11-Chloro-2,3,4,5-tetrahydro-1H-azepino[4,3-b]quinoline dihydrochloride was prepared by hydrolysis of 2-acetyl-11-chloro-2,3,4,5-tetrahydro-1H-azepino[4,3-b]quinoline hydrochloride with 2 N hydrochloric acid. Yield of the dihydrochloride: 11% of theory; m.p. 260° C. (decomp.).

EXAMPLE 13

11-Chloro-1,2,4,5-tetrahydro-3H-azepino[4,5-b]quinoline dihydrochloride was prepared by hydrolysis of 11-chloro-3-phenoxycarboxyl-1,2,4,5-tetrahydro-3H-azepino[4,5-b]quinoline or 11-chloro-3-ethoxycarbonyl-1,2,4,5-tetrahydro-3H-azepino[4,5-b]quinoline with concentrated hydrochloric acid. Yield of the dihydrochloride: 69% of theory; m.p. 261° C. (decomp.).

EXAMPLE 14

11-Hydroxy-1,2,3,4-tetrahydro-3H-azepino[4,5-b]quinoline dihydrochloride was prepared by hydrolysis of 11-hydroxy-3-phenoxycarbonyl-1,2,4,5-tetrahydro-3H-azepino[4,5-b]quinoline or 3-ethoxycarbonyl-11-hydroxy-1,2,4,5-tetrahydro-3H-azepino [4,5-b]quinoline with concentrated hydrochloric acid. Yield of the dihydrochloride: 81% of theory; m.p. 295° C. (decomp.).

EXAMPLE 15

11-Hydroxy-2,3,4,5-tetrahydro-1H-azepino[4,3-b]quinoline dihydrochloride was prepared by hydrolysis of 11-hydroxy-2-phenoxycarbonyl-2,3,4,5-tetrahydro-1H-azepino[4,3-b]quinoline with concentrated hydrochloric acid. Yield of the dihydrochloride: 65% of theory; m.p. 289° C. (decomp.).

EXAMPLE 16

3-Benzyl-1,2,4,5-tetrahydro-11-methyl-3H-azepino[4,5-b] quinoline, 2-benzyl-2,3,4,5-tetrahydro-11-methyl-1H-azepino [4,3-b]quinoline and their dihydrochlorides 11 gm (54 millimols) of 1-benzyl-hexahydro-azepinone-(4) were dissolved in 100 ml of toluene, 18.6 gm (108 millimols) of p-toluenesulfonic acid and 7.3 gm (54 millimols) of 2-aminoacetophenone were added to the solution, and the mixture was heated at its boiling point for six hours. The water formed during the reaction was distilled off azeotropically and separated by means of a water trap. The precipitated salt was suction-filtered off after cooling, dissolved in 2 N sodium hydroxide and extracted with chloroform. After drying over sodium sulfate and distilling off the chloroform, 15 gm (92% of theory) of an isomeric mixture of the [4,5-b]- and [4,3-b]-isomers (ratio 4:6) were obtained as an oil.

For separation of the isomers, 15 gm of the isomeric mixture were dissolved in 20 ml of ethyl acetate and purified by chromatography on a silicagel column (diameter: 3.5 cm; height: 120 cm; grain size: 0.05 to 2 mm) with ethyl acetate as the eluant. The separation was thin-layer chromatographically monitored. The fractions containing only one of the respective isomers were combined and the ethyl acetate was distilled off, yielding 4 gm (24.5% of theory) of the [4,5-b]-isomer, m.p. 110° C., and 6 gm (36.8% of theory) of the [4,3-b]-isomer, m.p. 126° C. For conversion into the dihydrochlorides the isolated bases were dissolved in hot isopropanol, and isopropanolic hydrochloric acid was added.

Yield of the dihydrochloride of the [4,5-b]-isomer: 90 to 95% of theory; m.p. 255° C. (decomp.).

Yield of the dihydrochloride of the [4,3-b]-isomer: 90 to 95% of theory; m.p. 244° C. (decomp.).

EXAMPLE 17

1,2,4,5-Tetrahydro-3,11-dimethyl-3H-azepino[4,5-b]quinoline, 2,3,4,5-tetrahydro-2,11-dimethyl-1H-azepino[4,3-b]quinoline and their dihydrochlorides were prepared from 1-methyl-hexahydro-azepinone-(4) hydrochloride and 2-amino-acetophenone analogous to Example 1.

Yield of the dihydrochloride of the [4,5-b]-isomer: 19% of theory; m.p. 282° C. (decomp.).

Yield of the dihydrochloride of the [4,3-b]-isomer: 39% of theory; m.p. 280° C. (decomp.).

EXAMPLE 18

3-Ethyl-1,2,4,5-tetrahydro-11-methyl-3H-azepino[4,5-b]quinoline, 2-ethyl-2,3,4,5-tetrahydro-11-methyl-1H-azepino[4,3-b]quinoline and their dihydrochlorides were prepared from 1-ethyl-hexahydro-azepinone-(4) hydrochloride and 2-aminoacetophenone analogous to Example 1. For the column chromatography acetone was used as the eluant.

Yield of the dihydrochloride of the [4,5-b]-isomer: 8% of theory; m.p. 274° C. (decomp.).

Yield of the dihydrochloride of the [4,3-b]-isomer: 10% of theory; m.p. 278° C. (decomp.).

EXAMPLE 19

1,2,4,5-Tetrahydro-11-methyl-3-propyl-3H-azepino[4,5-b]quinoline, 2,3,4,5-tetrahydro-11-methyl-2-propyl-1H-azepino [4,3-b]quinoline and their dihydrochlorides were prepared from 1-propyl-hexahydro-azepinone-(4) hydrochloride and 2-aminoacetophenone analogous to Example 1.

Yield of the dihydrochloride of the [4,5-b]-isomer: 10% of theory; m.p. 246° (decomp.).

Yield of the dihydrochloride of the [4,3-b]-isomer: 18% of theory; m.p. 232° C. (decomp.).

EXAMPLE 20

1,2,4,5-Tetrahydro-3-isopropyl-11-methyl-3H-azepino[4,5-b]quinoline, 2,3,4,5-tetrahydro-2-isopropyl-11-methyl-1H-azepino[4,3-b]quinoline and their dihydrochlorides were prepared from 1-isopropyl-hexahydro-azepinone-(4) hydrochloride and 2-aminoacetophenone analogous to Example 1.

Yield of the dihydrochloride of the [4,5-b]-isomer: 33% of theory; m.p. 281° C. (decomp.).

Yield of the dihydrochloride of the [4,3-b]-isomer: 60% of theory; m.p. 273° C. (decomp.).

EXAMPLE 21

3-Butyl-1,2,4,5-tetrahydro-11-methyl-3H-azepino[4,5-b]quinoline, 2-butyl-2,3,4,5-tetrahydro-11-methyl-1H-azepino [4,3-b]quinoline and their dihydrochlorides were prepared from 1-butyl-hexahydro-azepinone-(4) hydrochloride and 2-amino-acetophenone analogous to Example 1. For the column-chromatographic separation ethyl acetate was used as the eluant.

Yield of the dihydrochloride of the [4,5-b]-isomer: 8% of theory; m.p. 251° C. (decomp.).

Yield of the dihydrochloride of the [4,3-b]-isomer: 12% of theory; m.p. 245° C. (decomp.).

EXAMPLE 22

1,2,4,5-Tetrahydro-3-isobutyl-11-methyl-3H-azepino[4,5-b]quinoline, 2,3,4,5-tetrahydro-2-isobutyl-11-methyl-1H-azepino[4,3-b]quinoline and their dihydrochlorides were prepared from 1-isobutyl-hexahydro-azepinone-(4) hydrochloride and 2-amino-acetophenone analogous to Example 1, except that the isomeric mixture of the bases was not separated chromatographically, but converted into the mixture of isomeric dihydrochlorides in isopropanol with isopropanolic hydrochloric acid. By hot extraction in a Soxhlet apparatus with acetone the dihydrochloride of the [4,3-b]-isomer was preferentially extracted, while the corresponding [4,5-b]-isomer remained undissolved. Upon cooling or evaporation of the acetone, the [4,3-b]-isomer crystallized out.

Yield of the dihydrochloride of the [4,5-b]-isomer: 12% of theory; m.p. 242° C. (decomp.).

Yield of the dihydrochloride of the [4,3-b]-isomer: 8% of theory; m.p. 235° C. (decomp.).

EXAMPLE 23

DL-3-sec.Butyl-1,2,4,5-tetrahydro-11-methyl-3H-azepino[4,5-b]quinoline, DL-2-sec.butyl-2,3,4,5-tetrahydro-11-methyl-1H-azepino[4,3-b]quinoline and their dihydrochlorides were prepared from DL-sec.butyl-hexahydro-azepinone-(4) hydrochloride and 2-amino-acetophenone analogous to Example 1.

Yield of the dihydrochloride of the [4,5-b]-isomer: 30% of theory; m.p. 260° C. (decomp.).

Yield of the dihydrochloride of the [4,3-b]-isomer: 56% of theory; m.p. 280° C. (decomp.).

EXAMPLE 24

3-tert.Butyl-1,2,4,5-tetrahydro-11-methyl-3H-azepino[4,5b]quinoline, 2-tert.butyl-2,3,4,5-tetrahydro-11-methyl-1H-azepino[4,3-b]quinoline and their dihydrochlorides were prepared from 1-tert.butyl-hexahydro-azepinone-(4) hydrochloride and 2-amino-acetophenone analogous to Example 1.

Yield of the dihydrochloride of the [4,5-b]-isomer: 11% of theory; m.p. 301° C. (decomp.).

Yield of the dihydrochloride of the [4,3-b]-isomer: 10% of theory; m.p. 270° C. (decomp.).

EXAMPLE 25

1,2,4,5-Tetrahydro-5,11-dimethyl-3H-azepino[4,5-b]azepine and its dihydrochloride were prepared from 3-methyl-hexahydro-azepinone-(4) hydrochloride and 2-amino-acetophenone analogous to Example 1. The [4,3-b]-isomer did not form, so that no separation of the isomers was necessary. Yield of the dihydrochloride: 36% of theory; m.p. 250° C. (decomp.).

EXAMPLE 26

3-Benzyl-1,2,4,5-tetrahydro-3H-azepino[4,5-b]quinoline dihydrochloride and 2-benzyl-2,3,4,5-tetrahydro-3H-azepino [4,3-b]quinoline 15 gm (124 millimols) of 2-amino-benzaldehyde and 29.8 gm (124 millimols) of 1-benzyl-hexahydro-azepinone-(4) hydrochloride were dissolved in 360 ml of methanol, 2.95 gm (124 millimols) of sodium hydroxide were added, and the mixture was stirred at room temperature for 24 hours under exclusion of light. Thereafter, the methanol was distilled off, the residue was dissolved in chloroform to separate the sodium chloride, and the solution was filtered and evaporated. Upon recrystallization of the evaporation residue from isopropanol and ethanol, the [4,3-b]-isomer was obtained. The isopropanolic mother liquor was admixed with isopropanolic hydrochloric acid, and the precipitated dihydrochloride of the [4,5-b]-isomer was recrystallized from ethanol.

Yield of the dihydrochloride of the [4,5-b]-isomer: 10% of theory; m.p. 252° C. (decomp.).

Yield of the [4,3-b]-isomer: 21% of theory; m.p. 134° C.

EXAMPLE 27

1,2,4,5-Tetrahydro-3-(p-methyl-benzyl)-3H-azepino[4,5-b]quinoline dihydrochloride and 2,3,4,5-tetrahydro-2-(p-methylbenzyl)-1H-azepino[4,3-b]quinoline dihydrochloride were prepared from 1-(p-methyl-benzyl)-hexahydro-azepinone-(4) hydrochloride and 2-amino-benzaldehyde analogous to Example 26 in methanol/water (1:1). For separation of the isomers, the obtained isomeric mixture was converted into the mixture of isomeric dihydrochlorides in isopropanol with isopropanolic hydrochloric acid. Upon recrystallization from methanol, only the dihydrochloride of the [4,5-b]-isomer crystallized out. The mother liquor was evaporated to dryness, and after treatment with ethanol the dihydrochloride of the [4,3-b]-isomer was obtained.

Yield of the dihydrochloride of the [4,5-b]-isomer: 7% of theory; m.p. 263° C.

Yield of the dihydrochloride of the [4,3-b]-isomer: 19% of theory; m.p. 208° C.

EXAMPLE 28

3-Ethyl-9-chloro-1,2,4,5-tetrahydro-11-phenyl-3H-azepino [4,5-b]quinoline dihydrochloride and 2-ethyl-9-chloro-2,3,4,5-tetrahydro-11-phenyl-1H-azepino[4,3-b]quinoline dihydrochloride were prepared from 1-ethyl-hexahydro-azepinone-(4) hydrochloride and 2-amino-5-chloro-diphenyl ketone analogous to Example 1. The reaction was carried out in 2 N hydrochloric acid/dioxane (2:1). Acetone was used as eluant for chromatographic separation of the isomers.

Yield of the dihydrochloride of the [4,5-b]-isomer: 26% of theory; m.p. 280° C. (decomp.).

Yield of the dihydrochloride of the [4,3-b]-isomer: 44% of theory; m.p. 278° C. (decomp.).

EXAMPLE 29

3-Ethyl-1,2,4,5-tetrahydro-11-phenyl-3H-azepino[4,5-b]quinoline dihydrochloride and 2-ethyl-2,3,4,5-tetrahydro-11-phenyl-1H-azepino[4,3-b]quinoline dihydrochloride were prepared from 1- ethyl-hexahydro-azepinone-(4) hydrochloride and 2-amino-benzophenone analogous to Example 28.

Yield of the dihydrochloride of the [4,5-b]-isomer: 28% of theory; m.p. 280° C. (decomp.).

Yield of the dihydrochloride of the [4,3-b]-isomer: 50% of theory; m.p. 273° C. (decomp.).

EXAMPLE 30

3-Benzyl-1,2,4,5-tetrahydro-11-phenyl-3H-azepino[4,5-b]quinoline dihydrochloride and 2-benzyl-2,3,4,5-tetrahydro-11-phenyl-1H-azepino[4,3-b]quinoline dihydrochloride were prepared from 1-benzyl-hexahydro-azepinone-(4) hydrochloride and 2-amino-benzophenone analogous to Example 28.

Yield of the dihydrochloride of the [4,5-b]-isomer: 26% of theory; m.p. 250° C. (decomp.).

Yield of the dihydrochloride of the [4,3-b]-isomer: 49% of theory; m.p. 248° C.

EXAMPLE 31

9-Chloro-1,2,4,5-tetrahydro-11-phenyl-3H-azepino[4,5-b]quinoline dihydrochloride and 9-chloro-2,3,4,5-tetrahydro-11-phenyl-1H-azepino[4,3-b]quinoline dihydrochloride were prepared from hexahydroazepinone-(4) hydrochloride and 2-amino-5-chloro-diphenyl ketone analogous to Example 28.

Yield of the dihydrochloride of the [4,5-b]-isomer: 43% of theory; m.p. 278° C. (decomp.).

Yield of the dihydrochloride of the [4,3-b]-isomer: 34% of theory; m.p. >320° C.

EXAMPLE 32

3-Ethyl-11-cyclohexyl-1,2,4,5-tetrahydro-3H-azepino[4,5-b]quinoline and
2-ethyl-11-cyclohexyl-2,3,4,5-tetrahydro-1H-azepino[4,3-b]quinoline and their dihydrochlorides by method A A mixture consisting of 1.77 gm (10 millimols) of 1-ethyl-hexhydroazepinone-4) hydrochloride, 2 gm (10 millimols) of 2-aminophenyl cyclohexyl ketone and 40 ml of phosphorus oxychloride was heated at its boiling point for 2.5 hours, and subsequently the excess phosphorus oxychloride was distilled off. The distillation residue was taken up in ice water, and the aqueous mixture was made alkaline with sodium hydroxide and extracted with chloroform. The chloroform extracts were dried over sodium sulfate and evaporated, and the residue was dissolved in methanol and purified by chromatography on a silicagel column (diameter: 2 cm; height: 80 cm; grain size: 0.05 to 0.2 mm) with methanol as the eluant for separation of the isomers. The [4,3-b]-isomer was converted into its dihydrochloride in acetone with isopropanolic hydrochloric acid.

Yield of the [4,5-b]-isomer: 15% of theory; m.p. 104° C.

Yield of the dihydrochloride of the [4,3-b]-isomer: 45% of theory; m.p. 255° C.

EXAMPLE 33

3-Ethyl-11-chloro-1,2,4,5-tetrahydro-3H-azepino[4,5-b]quinoline,
2-ethyl-11-chloro-2,3,4,5-tetrahydro-1H-azepino[4,3-b]quinoline and their dihydrochlorides by method A A mixture consisting of 100 gm (0.563 mol) of 1-ethyl-hexahydroazepinone-(4) hydrochloride, 500 ml of phosphorus oxychloride and 72.5 gm (0.563 mol) of anthranilic acid was boiled for 4 hours. After cooling, the mixture was decomposed with ice, made alkaline and extracted with chloroform. For separation, the isomeric mixture was purified by chromatography on silicagel with ethanol as the eluant. By precipitation with ethanolic hydrochloric acid, the isomers were obtained in the form of their dihydrochlorides.

Yield of the dihydrochloride of the [4,3-b]-isomer: 45% of theory; m.p. 267° C. (decomp.).

Yield of the dihydrochloride of the [4,5-b]isomer: 16% of theory; m.p. 233° to 236° C. (decomp.).

EXAMPLE 34

3-Benzyl-11-chloro-1,2,4,5-tetrahydro-3H-azepino[4,5-b]quinoline dihydrochloride and
2-benzyl-11-chloro-2,3,4,5-tetrahydro-1H-azepino[4,3-b]quinoline by method A A mixture consisting of 135 gm (0.563 mol) of 1-benzyl-hexahydroazepinone-(4) hydrochloride, 77.5 gm (0.563 mol) of anthranilic acid and 500 ml of phosphorus oxychloride was boiled for 3 hours. Then, the mixture was decomposed with ice water, made alkaline and extracted with chloroform. After evaporation of the chloroform extract, the residue was recrystallized from isopropanol.

Yield of the [4,3-b]-isomer: 33% of theory; m. p. 148° C. The [4,5-b]-isomer was obtained as its dihydrochloride by precipitation from the mother liquor with isopropanolic hydrochloric acid.

Yield: 31% of theory; m.p. 220° C. (decomp.).

EXAMPLE 35

3-Ethyl-11-hydroxy-1,2,4,5-tetrahydro-3H-azepino[4,5-b]quinoline dihydrochloride and
2-ethyl-11-hydroxy-2,3,4,5-tetrahydro-1H-azepino[4,3-b]quinoline dihydrochloride by method A A mixture consisting of 6.85 gm (50 millimols) of anthranilic acid, 8.9 gm (50 millimols) of 1-ethyl-hexahydroazepinone-(4) hydrochloride and 300 gm of polyphosphoric acid was stirred at 160° C. for 3 hours. Thereafter, the mixture was poured over ice, made alkaline and extracted with chloroform. The isomeric mixture thus obtained was separated by column chromatography on silicagel with chloroform/methanol (1:1) as the eluant. The isomers were isolated as their dihydrochlorides from solution in ethanol by addition of ethanolic hydrochloric acid.

Yield of the dihydrochloride of the [4,5-b]-isomer: 13% of theory; m.p. 295° C. (decomp.).

Yield of the dihydrochloride of the [4,3-b]-isomer: 6% of theory; m.p. 294° C. (decomp.).

EXAMPLE 36

3-Benzyl-11-hydroxy-1,2,4,5-tetrahydro-3H-azepino[4,5-b]quinoline and
2-benzyl-11-hydroxy-2,3,4,5-tetrahydro-1H-azepino[4,3-b]quinoline by method A A mixture consisting of 135 gm (0.563 mol) of 1-benzyl-hexahydroazepinone-(4) hydrochloride, 77.5 gm (0.563 mol) of anthranilic acid and 1200 gm of polyphosphoric acid was stirred at 160° C. for 5 hours. The mixture was then poured over ice, made alkaline and extracted with chloroform. After evaporation of the combined chloroform extracts, the residue was recrystallized from ethanol.

Yield of the [4,5-b]-isomer- 10.4% of theory; m.p. 274° C. The [4,3-b]-isomer was obtained by evaporation of the mother liquor and repeated recrystallization of the evaporation residue from methanol.

Yield: 20% of theory; m.p. 258° C.

EXAMPLE 37

1,2,4,5-Tetrahydro-11-methyl-3H-azepino[4,5-b]quinoline dihydrochloride and 2,3,4,5-tetrahydro-11-methyl-1H-azepino[4,3-b]quinoline Stoichiometric quantities (25 millimols) of hexahydro-azepinone-(4) hydrochloride and 2-aminoacetophenone hydrochloride were carefully comminuted, admixed and heated to a temperature of 120° C, whereby the mixture melted. The temperature was held for 30 minutes between 120° and 140° C. by cooling or heating, as required. During that time the molten mass crystallized. After cooling, the crystals were dissolved in water, and the solution was made alkaline with sodium hydroxide and then extracted with chloroform.

Yield of the raw isomeric mixture: 98% of theory. The separation of the isomers was carried out as described in Example 1.

Yield of the dihydrochloride of the [4,5-b]-isomer: 43% of theory; m.p. 296° C.

Yield of the base of the [4,3-b]-isomer: 32% of theory; m.p. 122° C.

EXAMPLE 38

9-Bromo-1,2,4,5-tetrahydro-11-methyl-3H-azepino[4,5-b]quinoline, 9-bromo-2,3,4,5-tetrahydro-11-methyl-1H-azepino[4,5-b]quinoline and their dihydrochlorides were prepared from hexahydro-azepinone-(4) hydrochloride and 2-amino-5-bromoacetophenone analogous to Example 1.

Yield of the dihydrochloride of the [4,5-b]-isomer: 21% of theory; m.p. 313° C. (decomp.).

Yield of the dihydrochloride of the [4,3-b]-isomer: 22% of theory; m.p. 307° C. (decomp.).

EXAMPLE 39

9-Chloro-1,2,4,5-tetrahydro-11-methyl-3H-azepino[4,5-b]quinoline, 9-chloro-2,3,4,5-tetrahydro-11-methyl-1H-azepino[4,3-b]quinoline and their dihydrochlorides were prepared from hexahydro-azepinone-(4) hydrochloride and 2-amino-5-chloroacetophenone analogous to Example 1.

Yield of the dihydrochloride of the [4,5-b]-isomer: 19% of theory; m.p. 300° C. (decomp.).

Yield of the dihydrochloride of the [4,3-b]-isomer: 30% of theory; m.p. 288° C. (decomp.).

EXAMPLE 40

10-Chloro-1,2,4,5-tetrahydro-11-methyl-3H-azepino[4,5-b]quinoline dihydrochloride 2.5 gm (9.3 millimols) of 3-acetyl-10-amino-11-methyl-1,2,4,5-tetrahydro-3H-azepino[4,5-b]quinoline, dissolved in a mixture of 6 ml of concentrated hydrochloric acid and 42 ml of water, were diazotized with a solution of 0.79 gm (11.5 millimols) of sodium nitrite in 12 ml of water at 0° C. The resulting diazonium salt solution was added dropwise to a solutin of 3.9 gm of copper(I) chloride in 80 ml of semi-concentrated hydrochloric acid, and the resulting mixture was heated at 60° C. for 20 minutes and then at its boiling point for 6 hours. Thereafter, the cooled solution was made alkaline with sodium hydroxide and was then extracted with chloroform. After drying the chloroform extract over sodium sulfate, the chloroform was distilled off, and the residual dihydrochloride was recrystallized from isopropanol.

Yield of the dihydrochloride: 30% of theory; m.p. 285° C. (decomp.).

EXAMPLE 41

7-Chloro-1,2,4,5-tetrahydro-11-methyl-3H-azepino[4,5-b]quinoline dihydrochloride was prepared from 3-acetyl-7-amino-1,2,4,5-tetrahydro-11-methyl-3H-azepino[4,5-b]quinoline analogous to Example 40.

Yield of the dihydrochloride: 18% of theory; m.p. 245° C. (decomp.).

EXAMPLE 42

1,2,4,5-Tetrahydro-11-methyl-9-nitro-3H-azepino[4,5-b]quinoline, 2,3,4,5-tetrahydro-11-methyl-9-nitro-1H-azepino[4,3-b]quinoline and their dihydrochlorides by method A A mixture consisting of 4.5 gm (25 millimols) of 2-amino-5-nitro-acetophenone, 3.8 gm (25 millimols) of hexahydroazepinone-(4) hydrochloride and 50 ml of phosphorus oxychloride was heated at its boiling point for three hours, and thereafter the excess phosphorus oxychloride was distilled off in a water aspirator vacuum. The distillation residue was taken up in water, and the resulting solution was made alkaline with sodium hydroxide and then exhaustively extracted with chloroform. After drying the chloroform extract over sodium sulfate, filtering it and distilling off the chloroform, the residual mixure of isomeric bases was separated by chromatography on a silicagel column (diameter: 3 cm; height: 120 cm; grain size: 0.05 to 0.2 mm) with methanol as the eluant. The separation of the isomers was thin-layer chromatographically monitored. The fractions containing only one of the respective isomers were combined, he methanol was distilled off, and each isomer was converted into its dihydrochloride in acetone with isopropanolic hydrochloric acid.

Yield of the dihydrochloride of the [4,5-b]-isomer: 30% of theory; m.p. 308° C. (decomp.).

Yield of the dihydrochloride of the [4,3-b]-isomer: 15% of theory; m.p. 308° C. (decomp.).

EXAMPLE 43

1,2,4,5-Tetrahydro-11-methyl-8-nitro-3H-azepino[4,5-b] quinoline, 2,3,4,5-tetrahydro-11-methyl-8-nitro-1H-azepino [4,3-b]quinoline and their dihydrochlorides were prepared from hexahydro-azepinone-(4) hydrochloride and 2-amino-4-nitro-acetophenone analogous to Example 42.

Yield of the dihydrochloride of the [4,5-b]-isomer: 20% of theory; m. p. 284° C. (decomp.).

Yield of the dihydrochloride of the [4,3-b]-isomer: 22% of theory; m.p. 300° C. (decomp.).

EXAMPLE 44

1,2,4,5-Tetrahydro-11-methyl-7-nitro-3H-azepino[4,5-b] quinoline and 2,3,4,5-tetrahydro-11-methyl-7-nitro-1H-azepino[4,3-]quinoline were prepared from hexahydroazepinone-(4) hydrochloride and 2-amino-3-nitro-acetophenone analogous to Example 42.

Yield of the [4,5-b]-isomer: 15% of theory, m.p. 130° C.

Yield of the [4,3-b]-isomer: 18% of theory; m.p. 127° C.

EXAMPLE 45

1,2,4,5-Tetrahydro-11-methyl-10-nitro-3H-azepino[4,5-b] quinoline, 2,3,4,5-tetrahydro-11-methyl-10-nitro-1H-azepino[4,3-b]quinoline and their dihydrochloides were prepared from hexahydro-azepinone-(4) hydrochloride and 2-amino-6-nitro-acetophenone analogous to Example 42.

Yield of the dihydrochloride of the [4,5-b]-isomer: 18% of theory; m.p. 190° C. (decomp.).

Yield of the dihydrochloride of the [4,3-b]-isomer: 19% of theory; m.p. 210° C. (decomp.).

EXAMPLE 46

1,2,4,5-Tetrahydro-11-methyl-7-nitro-3H-azepino[4,5-b] quinoline, 1,2,4,5-tetrahydro-11-methyl-8-nitro-3H-azepino [4,5-b]quinoline and 1,2,4,5-tetrahydro-11-methyl-10-nitro-3H-azepino[4,5-b]quinoline 35 gm (160 millimols) of 1,2,4,5-tetrohydro-11-methyl-3H-azepino[4,5-b]quinoline were dissolved in 115 ml of concentrated sulfuric acid, and nitrated at −5 to 0° C. with a mixture of 26.8 gm of fuming nitric acid (density = 1.5) and 37 gm of concentrated sulfuric acid (density = 1.83). After standing for two hours at 0° C., the reaction mixture was poured over ice, and the aqueous solution was made alkaline with concentrated sodium hydroxide and was then exhaustively extracted with chloroform. After drying the extract and distilling off the chloroform, 75% of theory of an isomeric mixture of the 7-nitro, 8-nitro and 10-nitro compounds (ratio = 43:7:21) was obtained. To separate the isomers, the isomeric mixture was either converted into the 3-acetyl- (with acetic acid anhydride analogous to Example 109) or into the 3-carboxylic acid ethyl ester derivatives (with chloroformic acid ethyl ester analogous to Example 63).

The 7-nitro-3-acetyl-compound was obtained by recrystallization from ethyl acetate. To separate the 8- and 10-nitro-3-acetyl-compounds, the ethyl acetate mother liquor evaporation residue was chromatographed on a silicagel column with ethyl acetate:acetone as the eluant. In the same manner, the 7-, 8- and 10-nitro-3-carboxylic acid ethyl ester compounds were separated.

7-Nitro-3-acetyl derivative; yield: 34.6% of theory; m.p. 187° C.

8-Nitro-3-acetyl derivative; yield: 10.7% of theory; m.p. 173° C.

10-Nitro-3-acetyl derivative; yield: 18.2% of theory; m.p. 155° C.

7-Nitro-3-carboxylic acid ethyl ester derivative; yield: 36% of theory; m.p. 175° C.

8-Nitro-3-carboxylic acid ethyl ester derivative; yield: 8% of theory; m.p. 168° C.

10-Nitro-3-carboxylic acid ethyl ester derivative; yield: 20% of theory; m.p. 149° C.

The corresponding 3H compounds were obtained from these compounds by alkaline or acid hydrolysis with a yield of 80 to 90%.

EXAMPLE 47

9-Amino-1,2,4,5-tetrahydro-11-methyl-3H-azepino[4,5-b]quinoline and its trihydrochloride were prepared from 1,2,4,5-tetrahydro-11-methyl-9-nitro-3H-azepino[4,5-b]quinoline by hydrogenation in methanol, with Raney nickel as the catalyst, at room temperaure and at a hydrogen pressure of 5 atmospheres, and conversion of the base into its trihydrochloride. Yield of the trihydrochloride: 75% of theory; m.p. 320° C. (decomp.).

EXAMPLE 48

9-Amino-2,3,4,5-tetrahydro-11-methyl-1H-azepino[4,3-b]quinoline and its trihydrochloride were prepared from 2,3,4,5-tetrahydro-11-methyl-9-nitro-1H-azepino[4,3-b]quinoline analogous to Example 47. Yield of he trihydrochloride: 70% of theory; m. p. 240° C.

EXAMPLE 49

3 - Acetyl - 7 - amino - 1,2,4,5,tetrahydro - 11 - methyl - 3H - azepino[4,5 - b]quinoline was prepared from 3 - acetyl - 1,2,4,5 - tetrahydro - 11 - methyl - 7 - nitro - 3H-azepino[4,5-b]quinoline (m.p. 186° C.) by catalytical hydrogenation at 5 atmospheres of hydrogen pressure in methanol at room temperature with Raney-nickel as the catalyst. Yield: 73% of theory; m.p. 129° C.

EXAMPLE 50

7-Amino-1,2,4,5-tetrahydro-11-methyl-3H-azepino[4,5-b]quinoline and its dihydrochloride were prepared by hydrolysis with 2 N sodium hydroxide of 3-acetyl-7-amino-1,2,4,5-tetrahydro-11-methyl-3H-azepino[4,5-b]quinoline, and subsequent conversion of the base into its dihydrochloride. Yield of the dihydiochloride: 83%; of theory; m.p. 285° C. (decomp.).

EXAMPLE 51

3-Acetyl-10-amino-1,2,4,5-tetrahydro-11-methyl-3H-azepino[4,5-b]quinoline was prepared by catalytic hydrogenation of the corresponding 10-nitro-compound analogous to Example 49. Yield: 70% of theory; m.p. 150° C.

EXAMPLE 52

10-Amino-1,2,4,5-tetrahydro-11-methyl-3H-azepino[4,5-b]quinoline dihydrochloride hydrate was prepared from the corresponding 3-acetyl-substituted compound by acid hydrolysis. Yield: 13% of theory; m.p. 300° C. (decomp.).

EXAMPLE 53

1,2,4,5-Tetrahydro-9-hydroxy-11-methyl-3H-azepino[4,5-b]quinoline, 2,3,4,5-tetrahydro-9-hydroxy-11-methyl-1H-azepino[4,3-b]quinoline and their dihydrochlorides were prepared from hexahydro-azepinone-(4) hydrochloride and 2-amino-5-hydroxy-acetophenone analogous to Example 1.

Yield of the dihydrochloride of the [4,5-b]-isomer: 10% of theory; m.p. 230° C. (decomp.).

Yield of the dihydrochloride of the [4,3-b]-isomer: 20% of theory; m.p. 250° C. (decomp.).

EXAMPLE 54

1,2,4,5-Tetrahydro-7-hydroxy-11-methyl-3H-azepino[4,5-b]quinoline, 2,3,4,5-tetrahydro-7-hydroxy-11-methyl-1H-azepino[4,3-b]quinoline and their dihydrochlorides were prepared from hexahydro-azepinone-(4) hydrochloride and 2-amino-3-hydroxy-acetophenone analogous to Example 1.

Yield of the dihydrochloride of the [4,5-b]-isomer: 19.5% of theory; m.p. 300° C. (decomp.).

Yield of the dihydrochloride of the [4,3-b]-isomer: 23.5% of theory; m.p. 317° C. (decomp.).

EXAMPLE 55

3-Benzyl-1,2,4,5-tetrahydro-9-hydroxy-11-methyl-3H-azepino[4,5-b]quinoline, 2-benzyl-2,3,4,5-tetrahydro-9-hydroxy-11-methyl-1H-azepino[4,3-b]quinoline and their dihydrochlorides were prepared from 1-benzyl-hexahydro-azepinone-(4) hydrochloride and 2-amino-5-hydroxy-acetophenone analogous to Example 1.

Yield of the dihydrochloride of the [4,5-b]-isomer: 10% of theory; m.p. 278° C. (decomp.).

Yield of the dihydrochloride of the [4,3-b]-isomer: 20% of theory; m.p. 210° C. (decomp.).

EXAMPLE 56

1,2,4,5-Tetrahydro-11-methyl-9-methoxy-3H-azepino[4,5-b]quinoline, 2,3,4,5-tetrohydro-11-methyl-9-methoxy-1H-azepino[4,3-b]quinoline and their dihydrochlorides were prepared from hexahydro-azepinone-(4) hydrochloride and 2-amino-5-methoxy-acetophenone analogous to Example 1.

Yield of the dihydrochloride of the [4,5-b]-isomer: 10% of theory; m.p. 284° C. (decomp.).

Yield of the dihydrochloride of the [4,3-b]-isomer: 29% of theory; m.p. 274° C. (decomp.).

EXAMPLE 57

1,2,4,5-Tetrahydro-11-methyl-7-methoxy-3H-azepino[4,5-b]quinoline, 2,3,4,5-tetrahydro-11-methyl-7-methoxy-1H-azepino[4,3-b]quinoline and their dihydochlorides were prepared from hexahydro-azepinone-(4) hydrochloride and 2-amino-3-methoxy-acetophenone analogous to Example 1.

Yield of the dihydrochloride of the [4,5-b]-isomer: 19% of theory; m.p. 260° C. (decomp.).

Yield of the dihydrochloride of the [4,3-b]-isomer: 35% of theory; m.p. 224° C. (decomp.).

EXAMPLE 58

1,2,4,5-Tetrahydro-11-methyl-3-azepino[4,5-b]quinoline-carboxylic acid ethyl ester hydrochloride A solution of 146 gm (1.08 mol) of 2-aminoacetophenone in 2.5 liters of toluene was admixed with 186 gm (0.98 mol) of p-toluenesulfonic acid hydrate, and the mixture was heated at its boiling point, while the water formed by the reaction was azeotropically distilled off with the aid of a water trap, and over a period of 45 minutes 200 gm (1.08 mol) of hexahydro-azepinone-(4)-1-carboxylic acid ethyl ester were added dropwise. Subsequently, the resulting mixture was boiled for 6 hours. Upon cooling, the isomeric mixture of 1,2,4,5-tetrahydro-11-methyl-3-azepino [4,5-b]quinoline-carboxylic acid ethyl ester and 2,3,4,5-tetrahydro-11-methyl-1H-2-azepino[4,3-b]quinoline-carboxylic acid ethyl ester crystallized out (ratio 6:4) as their p-toluenesulfonates. After filtering off this isomeric mixture, aqueous 5% sodium hydroxide was added for liberation of the bases, and the mixture was extracted 4 times with 500 ml of chloroform each. After drying the combined extracts over sodium sulfate and distilling off the chloroform, 270 gm (88% of theory) of a mixture of the [4,5-b]-isomer and [4,3-b]-isomer was obtained (ratio 6:4). To separate the isomers, the isomeric mixture was recrystallized from ether (20 ml/gm of isomeric mixture) or ethyl acetate. The [4,5-b]-isomer crystallized out in pure form. Yield: 43.5% of theory; m.p. 124° C. For conversion into its hydochloride, 96 gm of 1,2,4,5-tetrahydro-11-methyl-3-azepino[4,5-b]quinoline-carboxylic acid ethyl ester were dissolved in 550 ml of hot isopropanol, the solution was filtered, and 100 of isopropanolic hydrochloric acid were added.

Yield: 93.5% of theory; m.p. 247° C. (decomp.).

EXAMPLE 59

1,2,4,5-Tetrahydro-11-methyl-3-azepino[4,5-b]quinoline-carboxylic acid ethyl ester 0.5 gm (1.7 millimols) of 3-benzyl-1,2,4,5-tetrahydro-11-methyl-3H-azepino[4,5-b]quinoline were reacted in 5 ml of methylene chloride with a stoichiometric quantity (0.15 ml) of ethyl chloroformate for four hours at room temperature. After distilling off the methylene chloride and recrystallizing the residue from ether, the product was obtained with a yield of 52% of theory; m.p. 125° C.

EXAMPLE 60

1,2,4,5-Tetrahydro-11-methyl-3-azepino[4,5-b]quinoline-carboxylic acid phenyl ester was prepared from 3-benzyl-1,2,4,5-tetrahydro-11-methyl-3H-azepino[4,5-b]quinoline and phenyl chloroformate analogous to Example 59.

Yield: 63% of theory; m.p. 150° C.

EXAMPLE 61

1,2,4,5-Tetrahydro-11-methyl-3-azepino[4,5-b]quinoline-carboxylic acid ethyl ester was prepared from 3-ethyl-1,2,4,5-tetrahydro 11-methyl-3H-azepino[4,5-b]quinoline and ethyl chloroformate analogous to Example 59.

Yield: 10% of theory; m.p. 125° C.

EXAMPLE 62

1,2,4,5-Tetrahydro-11-methyl-3-azepino[4,5-b]quinoline-carboxylic acid ethyl ester, 2,3,4,5-tetrahydro-11-methyl-2-azepino[4,3-b]quinoline-carboxylic acid ethyl ester and their hydrochlorides The isomeric mixture of the bases was prepared as described in Example 58. To separate the isomers, 1.2 gm of the [4,5-b]- and [4,3-b]-isomer mixture (ratio 6:4) were dissolved in 20 ml of hot isopropanol, and the solution was acidified with isopropanolic hydrochloric acid. The hydrochloride of the [4,5-b]-isomer crystallized out in pure form. After distilling the solvent out of the motor liquor and converting the residual hydrochloride into the base, the [4,3-b]-isomer was obtained from ether.

Yield of the hydrochloride of the [4,5-b]-isomer: 70% of theory; m.p. 247° C. (decomp.).

Yield of the hydrochloride of the [4,3-b]-isomer: 8% of theory; m.p. 219° C. (decomp.).

EXAMPLE 63

1,2,4,5-Tetrahydro-11-methyl-3-azepino[4,5-b]quinoline-carboxylic acid ethyl ester hydrochloride 11 gm (51.7 millimols) of 1,2,4,5-tetrahydro-11-methyl-3H-azepino[4,5-b]quinoline were dissolved in 275 ml of hot benzene, and then a solution of 9.8 ml (103.4 millimols) of ethyl chloroformate in 70 ml of benzene were simultaneously added dropwise. After refluxing the resulting mixture for 2 hours, 150 ml of ice water were added to the cooled reaction mixture, and the aqueous mixture was made alkaline with 2 N sodium hydroxide. The benzene layer was separated and the aqueous layer was extracted with chloroform. The combined benzene and chloroform phases were dried over sodium sulfate, the solvents were distilled off, and the residual oil was admixed with ether, whereupon 11 gm (75% of theory) of the base, m. p. 126° C., crystallized out. For conversion into the hydrochloride, 11 gm of the base were dissolved in 60 ml of isopropanol, the solution was filtered, and 10 ml of isopropanolic hydrochloric acid were added. The hydrochloride crystallized out of the hot solution. Yield: 12 gm (72% of theory); m.p. 247° C. (decomp.).

EXAMPLE 64

1,2,4,5-Tetrahydro-11-methyl-3-azepino[4,5-b]quinoline-carboxylic acid methyl ester hydrochloride was prepared analogous to Example 63 with methyl chloroformate.

Yield: 91% of theory; m.p. 245° C. (decomp.).

EXAMPLE 65

1,2,4,5-Tetrahydro-11-methyl-3-azepino[4,5-b]quinoline-carboxylic acid propyl ester hydrochloride was prepared analogous to Example 63 with propyl chloroformate.

Yield: 76% of theory; m.p. 243° to 245° C. (decomp.).

EXAMPLE 66

1,2,4,5-Tetrahydro-11-methyl-3-azepino[4,5-b]quinoline-carboxylic acid isopropyl ester hydrochloride was prepared analogous to Example 63 with isopropyl chloroformate.

Yield: 83% of theory; m.p. 227° C.

EXAMPLE 67

1,2,4,5-Tetrahydro- 11-methyl-3-azepino[4,5-b]quinoline-carboxylic acid butyl ester hydrochloride was prepared analogous to Example 63 with butyl chloroformate.

Yield: 77% of theory; m.p. 203° C. (decomp.).

EXAMPLE 68

1,2,4,5-Tetrahydro-11-methyl-3-azepino[4,5-b]quinoline-carboxylic acid isobutyl ester hydrochloride was prepared analogous to Example 63 with isobutyl chloroformate.

Yield: 83% of theory; m.p. 244° C. (decomp.).

EXAMPLE 69

DL-1,2,4,5-Tetrahydro-11-methyl-3-azepino[4,5-b]quinoline-carboxylic acid sec.butyl ester hydrochloride was prepared analogous to Example 63 with DL-sec.butyl chloroformate.

Yield: 87% of theory; m.p. 212° C. (decomp.).

EXAMPLE 70

1,2,4,5-Tetrahydro-11-methyl-3-azepino[4,5-b]quinoline-carboxylic acid cyclohexyl ester hydrochloride was prepared analogous to Example 63 with cyclohexyl chloroformate acid-cyclohexyl ester. Yield: 67% of theory; m.p. 233° C. (decomp.).

EXAMPLE 71

1,2,4,5-Tetrahydro-11-methyl-3-azepino[4,5-b]quinoline-carboxylic acid phenyl ester hydrochloride was prepared analogous to Example 63 with phenyl chloroformate.

Yield: 71% of theory; m.p. 246° C. (decomp.).

EXAMPLE 72

1,2,4,5-Tetrahydro-11-methyl-3-azepino[4,5-b]quinoline-carboxylic acid benzyl ester hydrochloride was prepared analogous to Example 63 with benzyl chloroformate.

Yield: 79% of theory; m.p. 199° C. (decomp.).

EXAMPLE 73

1,2,4,5-Tetrahydro-3-azepino[4,5-b]quinoline-carboxylic acid ethyl ester hydrochloride was prepared from 1,2,4,5-tetrahydro-3H-azepino[4,5-b]quinoline and ethyl chloroformate analogous to Example 63.

Yield: 64% of theory; m.p. 264° C. (decomp.).

EXAMPLE 74

1,2,4,5-Tetrahydro-11-ethyl-3-azepino[4,5-b]quinoline-carboxylic acid ethyl ester hydrochloride was prepared from 11-ethyl-1,2,4,5-tetrahydro-3H-azepino[4,5-b]quinoline and ethyl chloroformate analogous to Example 63.

Yield: 72% of theory; m.p. 212° C. (decomp.).

EXAMPLE 75

1,2,4,5-Tetrahydro-11-propyl-3-azepino[4,5-b]quinoline-carboxylic acid ethyl ester hydrochloride was prepared from 1,2,4,5-tetrahydro-11-propyl-3H-azepino[4,5-b]quinoline and ethyl chloroformate analogous to Example 63.

Yield: 84% of theory; m.p. 201° C. (decomp.).

EXAMPLE 76

9-Chloro-1,2,4,5-tetrahydro-11-phenyl-3-azepino[4,5-b]quinoline-carboxylic acid ethyl ester hydrochloride was prepared from 9-chloro-1,2,4,5-tetrahydro-11-phenyl-3H-azepino[4,5-b]quinoline and ethyl chloroformate analogous to Example 63.

Yield: 65% of theory; m.p. 238° C. (decomp.).

EXAMPLE 77

7-Chloro-1,2,4,5-tetrahydro-11-methyl-3-azepino[4,5-b]quinoline-carboxylic acid ethyl ester was prepared from 7-chloro-1,2,4,5-tetrahydro-11methyl-3H-azepino[4,5-b]quinoline and ethyl chloroformate analogous to Example 63.

Yield: 70% of theory; m.p. 169° C.

EXAMPLE 78

7-Hydroxy-1,2,4,5-Tetrahydro-11-methyl-3-azepino[4,5-b]quinoline-carboxylic acid ethyl ester hydrochloride was prepared from 7-hydroxy-1,2,4,5-tetrahydro-11-methyl-3H-azepino[4,5-b]quinoline and ethyl chloroformate analogous to Example 63, and subsequent hydrolysis of the intermediate 7-(ethoxycarbonyloxy)-1,2,4,5-tetrahydro-11-methyl-3-azepino[4,5-b]quinoline-carboxylic acid ethyl ester with dilute potassium hydroxide at 30° C.

Yield: 22% of theory; m.p. 129° C.

EXAMPLE 79

1,2,4,5-Tetrahydro-7-methoxy-11-methyl-3-azepino[4,5-b]quinoline-carboxylic acid ethyl ester hydrochloride was prepared from 1,2,4,5-tetrahydro-7-methoxy-11-methyl-3H-azepino[4,5-b]quinoline and ethyl chloroformate analogous to Example 63.

Yield: 49% of theory; m.p. 128° C.

EXAMPLE 80

1,2,4,5-Tetrahydro-11-methyl-7-nitro-3-azepino[4,5-b]quinoline-carboxylic acid ethyl ester hydrochloride was prepared from 1,2,4,5-tetrahydro-11-methyl-7-nitro-3H-azepino[4,5-b]quinoline and ethyl chloroformate analogous to Example 63.

Yield: 70% of theory; m.p. 242° C.

EXAMPLE 81

7-Amino-1,2,4,5-tetrahydro-11-methyl-3-azepino[4,5-b]quinoline-carboxylic acid ethyl ester hydrochloride was prepared from 1,2,4,5-tetrahydro-11-methyl-7-nitro-3-azepino[4,5-b]quinoline-carboxylic acid ethyl ester by catalytic hydrogenation in methanol at room temperature in the presence of Raney nickel.

Yield: 38% of theory; m.p. 168° C.

EXAMPLE 82

9-Bromo-1,2,4,5-tetrahydro-11-methyl-3-azepino[4,5-b]quinoline-carboxylic acid ethyl ester hydrochloride was prepared from 9-bromo-1,2,4,5-tetrahydro - 11 - methyl - 3H - azepino[4,5 - b]quinoline and ethyl chloroformate analogous to Example 63.

Yield: 62% of theory; m.p. 160° C.

EXAMPLE 83

9-Chloro-1,2,4,5-tetrahydro-11-methyl-3-azepino[4,5-b]quinoline-carboxylic acid ethyl ester hydrochloride was prepared from 9-chloro-1,2,4,5-tetrahydro-11-methyl-3H-azepino[4,5-b]quinoline and ethyl chloroformate analogous to Example 63.

Yield: 65% of theory; m.p. 238° C. (decomp.).

EXAMPLE 84

1,2,4,5-Tetrahydro-11-methyl-9-nitro-3-azepino[4,5-b]quinoline-carboxylic acid ethyl ester hydrochloride was prepared from 1,2,4,5-tetrahydro-11-methyl-9-nitro-3H-azepino[4,5-b]quinoline and ethyl chloroformate analogous to Example 63.

Yield: 51% of theory; m.p. 234° C. (decomp.).

EXAMPLE 85

1,2,4,5-Tetrahydro-9-methoxy-11-methyl-3-azepino[4,5-b]quinoline-carboxylic acid ethyl ester hydrochloride was prepared from 1,2,4,5-tetrahydro-9-methoxy-11-methyl-3H-azepino[4,5-b]quinoline and ethyl chloroformate analogous to Example 63.

Yield: 66% of theory; m.p. 142° C.

EXAMPLE 86

9-Hydroxy-1,2,4,5-tetrahydro-11-methyl-3-azepino[4,5-b]quinoline-carboxylic acid ethyl ester hydrochloride was prepared from 9-hydroxy-1,2,4,5-tetrahydro-11-methyl-3H-azepino[4,5-b]quinoline and ethyl chloroformate analogous to Example 63, followed by hydrolysis of the intermediate 9-(ethoxy-carbonyloxy)-1,2,4,5-tetrahydro-11-methyl-3-azepino[4,5-b]quinoline-carboxylic acid ethyl ester with dilute potassium hydroxide at 30° C.

Yield: 16% of theory; m.p. 284° C. (decomp.).

EXAMPLE 87

1,2,4,5-Tetrahydro-5,11-dimethyl-3-azepino[4,5-b]quinoline-carboxylic acid ethyl ester hydrochloride was prepared from 1,2,4,5-tetrahydro-5,11-dimethyl-3H-azepino[4,5-b]quinoline and ethyl chloroformate analogous to Example 63.

Yield: 84% of theory; m. p. 184° C.

EXAMPLE 88

5-(Ethoxy-carbonyloxy)-1,2,4,5-tetrahydro-11-methyl-3-azepino[4,5-]quinoline-carboxylic acid ethyl ester hydrochloride was prepared from 5-hydroxy-1,2,4,5-tetrahydro-11-methyl-3H-azepino[4,5-b]quinoline and ethyl chloroformate analogous to Example 63.

Yield: 73% of theory; m.p. 128° C.

EXAMPLE 89

1,2,4,5-Tetrahydro-8-hydroxy-11-methyl-3-azepino[4,5-b]quinoline-carboxylic acid ethyl ester and 2,3,4,5-tetrahydro-8-hydroxy-11-methyl-1H-2-azeino[4,3-b]quinoline-carboxylic acid ethyl ester were prepared from 1-ethoxy carbonyl-hexahydroazepinone-(4) and 2-amino-4-hydroxyacetophenone analogous to Example 16.

Yield of the [4,5-b]-isomer: 12% of theory; m.p. 263° C. (decomp.). Yield of the [4,3-b]-isomer: 8% of theory; m.p. 254° C. (decomp.).

EXAMPLE 90

9-Chloro-1,2,4,5-tetrahydro-11-phenyl-3-azepino[4,5-b]quinoline-carboxylic acid ethyl ester hydrochloride was prepared from 9-chloro-1,2,4,5-tetrahydro-11-phenyl-3H-azepino[4,5-b]quinoline and ethyl chloroformate analogous to Example 63.

Yield: 88% of theory; m.p. 216° C. (decomp.).

EXAMPLE 91

1,2,4,5-Tetrahydro-11-methyl-10-nitro-3-azepino[4,5-b]quinoline-carboxylic acid ethyl ester hydrochloride was prepared from 1,2,4,5-tetrahydro-11-methyl-10-nitro-3H-azepino[4,5-b]quinoline and ethyl chloroformate analogous to Example 63.

Yield: 78% of theory; m.p. 200° C. (decomp.).

EXAMPLE 92

10-Amino-1,2,4,5-tetrahydro-11-methyl-3-azepino[4,5-b]quinoline-carboxylic acid ethyl ester was prepared by reducing the corresponding 10-nitro compound (see Example 91) with tin-II-chloride in concentrated hydrochloric acid.

Yield: 26% of theory; m.p. 182° C.

EXAMPLE 93

5-Hydroxy-1,2,4,5-tetrahydro-11-methyl-3-azepino[4,5-b]quinoline-carboxylic acid ethyl ester hydrochloride was prepared from 5-(ethoxy-carbonyloxy)-1,2,4,5-tetrahydro-11-methyl-3-azepino[4,5-b]quinoline-carboxylic acid ethyl ester by hydrolysis with dilute sodium hydroxide at 30° to 50° C.

Yield: 70% of theory; m.p. 152° C.

EXAMPLE 94

2,3,4,5-Tetrahydro-11-methyl-1H-2-azepino[4,3-b]quinoline-carboxylic acid ethyl ester hydrochloride was prepared from 2,3,4,5-tetrahydro-11-methyl-1H-azepino[4,3-b]quinoline and ethyl chloroformate analogous to Example 63.

Yield: 58% of theory; m.p. 219° C. (decomp.).

EXAMPLE 95

2,3,4,5-Tetrahydro-1H-2-azepino[4,3-b]quinoline-carboxylic acid ethyl ester hydrochloride was prepared from 2,3,4,5-tetrahydro-1H-azepino[4,3-b]quinoline and ethyl chloroformate analogous to Example 63.

Yield: 81% of theory; m.p. 214° C. (decomp.).

EXAMPLE 96

5-(Ethoxy-carbonyloxy)-2,3,4,5-tetrahydro-1H-2-azepino[4,3-b]quinoline-carboxylic acid ethyl ester was prepared from 5-hydroxy-2,3,4,5-tetrahydro-1H-azepino[4,3-b]quinoline and ethyl chloroformate analogous to Example 63.

Yield: 80% of theory; m.p. <40° C.

EXAMPLE 97

9-Chloro-2,3,4,5-tetrahydro-11-phenyl-1H-2-azepino[4,3-b]quinoline-carboxylic acid ethyl ester hydrochloride was prepared from 9-chloro-2,3,4,5-tetrahydro-11-phenyl-1H-azepino[4,3-b]quinoline and ethyl chloroformate analogous to Example 63.

Yield: 89% of theory; m.p. 186° C.

EXAMPLE 98

11-Chloro-1,2,4,5-tetrahydro-3-azepino[4,5-b]quinoline-carboxylic acid phenyl ester A solution of 1.2 gm (7.7 millimols) of phenyl chloroformate in 20 ml of methylene chloride was added dropwise to a mixture of 2 gm (7.7 millimols) of 3-ethyl-11-chloro-1,2,4,5-tetrahydro-3H-azepino[4,5-b]quinoline and 15 ml of methylene chloride at 5° C. After standing overnight, the resulting mixture was diluted with ether to double its volume and was then suction-filtered. The filter cake was recrystallized from acetone.

Yield: 35.7% of theory; m.p. 157° C.

EXAMPLE 99

11-Chloro-1,2,4,5-tetrahydro-3-azepino[4,5-b]quinoline-carboxylic acid ethyl ester was prepared analogous to Example 98 from 3-benzyl-11-chloro-1,2,4,5-tetrahydro-3H-azepino[4,5-b]quinoline and ethyl chloroformate.

Yield: 97% of theory; m.p. 104° C.

EXAMPLE 100

11-Chloro-2,3,4,5-tetrahydro-1H-2-azepino[4,3-b]quinoline-carboxylic acid phenyl ester was prepared analogous to Example 98 from 2-ethyl-11-chloro-2,3,4,5-tetrahydro-1H-azepino[4,3-b]quinoline and phenyl chloroformate.

Yield: 18.5% of theory; m.p. 137° C.

EXAMPLE 101

11-Hydroxy-1,2,4,5-tetrahydro-3-azepino[4,5-b]quinoline-carboxylic acid phenyl ester 14 gm (89.4 millimols) of phenyl chloroformate were added dropwise to a mixture of 13.6 gm (44.7 millimols) of 3-benzyl-11-hydroxy-1,2,4,5-tetrahydro-3H-azepino[4,5-b]quinoline and 250 m. of methylene chloride at 5° C. After standing overnight, 5.8 gm (44.7 millimols) of N,N-diisopropyl-ethylamine were added, and the resulting mixture was stirred at room temperature for 6 hours. Subsequently, the reaction mixture was washed with water, dried over magnesium sulfate, and the methylene chloride was evaporated, whereby raw 11-(phenoxy-carbonyloxy)-1,2,4,5-tetrahydro-3-azepino[4,5-b]quinoline-carboxylic acid phenyl ester was obtained as the residue. The latter was heated in 250 ml of 1 N hydrochloric acid at 100° C. for 1 hour. Then, the mixture was made alkaline and was extracted with chloroform. The extract was evaporated, the residue was boiled briefly with acetone, and the mixture was suction-filtered.

Yield: 44% of theory; m.p. 232° C.

EXAMPLE 102

11-Hydroxy-1,2,4,5-tetrahydro-3-azepino[4,5-b]quinoline-carboxylic acid ethyl ester was prepared analogous to Example 101 from 3-benzyl-11-hydroxy-1,2,4,5-tetrahydro-3H-azepino[4,5-b]quinoline and ethyl chloroformate.

Yield: 20% of theory; m.p. 252° C.

EXAMPLE 103

11-Hydroxy-2,3,4,5-tetrahydro-1H-2-azepino[4,3-b]quinoline-carboxylic acid phenyl ester was prepared analogous to Example 101 from 2-benzyl-11-hydroxy-2,3,4,5-tetrahydro-1H-azepino[4,3-b]quinoline and phenyl chloroformate.

Yield: 51% of theory; m.p. 299° C.

EXAMPLE 104

3-Acetyl-1,2,4,5-tetrahydro-11-methyl-3H-azepino[4,5-b]quinoline hydrochloride was prepared from 1,2,4,5-tetrahydro-11-methyl-3H-azepino[4,5-b]quinoline and acetyl chloride analogous to Example 63.

Yield: 60% of theory; m.p. 210° C. (decomp.).

EXAMPLE 105

3-Acetyl-1,2,4,5-tetrahydro-11-phenyl-3H-azepino[4,5-b]quinoline hydrochloride was prepared from 1,2,4,5-tetrahydro-11-phenyl-3H-azepino[4,5-b]quinoline and acetyl chloride analogous to Example 63.

Yield: 90% of theory; m.p. 210° C. (decomp.).

EXAMPLE 106

3-(p-Chloro-benzoyl)-1,2,4,5-tetrahydro-11-methyl-3H-azepino[4,5-b]quinoline was prepared from 1,2,4,5-tetrahydro-11-methyl-3H-azepino[4,5-b]quinoline and 4-chloro-benzoyl chloride in pyridine.

Yield: 65% of theory; m.p. 163° C.

EXAMPLE 107

2-Acetyl-2,3,4,5-tetrahydro-11-methyl-1H-azepino[4,3-b]quinoline hydrochloride was prepared from 2,3,4,5-tetrahydro-11-methyl-1H-azepino[4,3-b]quinoline and acetyl chloride analogous to Example 63.

Yield: 75% of theory; m.p. 275° C. (decomp.).

EXAMPLE 108

2-Acetyl-5-hydroxy-11-methyl-2,3,4,5-tetrahydro-1H-azepino[4,3-b]quinoline hydrochloride was prepared from 5-hydroxy-11-methyl-2,3,4,5-tetrahydro-1H-azepino[4,3-b]quinoline and acetyl chloride analogous to Example 63, followed by hydrolysis of the intermediate 2-acetyl-5-acetoxy-2,3,4,5-tetrahydro-11-methyl-1H-azepino[4,3-b]quinoline with dilute sodium hydroxide.

Yield: 79% of theory; m.p. 150° C.

EXAMPLE 109

2-Acetyl-2,3,4,5-tetrahydro-11-phenyl-1H-azepino[4,3-b]quinoline hydrochloride was prepared from 2,3,4,5-tetrahydro-11-phenyl-1H-azepino[4,3-b]quinoline and acetic acid anhydride.

Yield: 92% of theory; m.p. 275° C. (decomp.).

EXAMPLE 110

2-Acetyl-11-chloro-2,3,4,5-tetrahydro-1H-azepino[4,3-b]quinoline hydrochloride 4.3 gm (55 millimols) of acetyl chloride were added dropwise to a mixture of 11.8 gm (50 millimols) of 11-chloro-2,3,4,5-tetrahydro-1H-azepino[4,3-b]quinoline, 5.5 gm. (55 millimols) of triethylamine and 300 ml of chloroform. After 100 hours of standing, the mixture was washed with water, and the chloroform phase was evaporated. The raw crystalline base was purified on a silicagel column with benzene/acetone (2:1) as the eluant. The hydrochloride was precipitated from isopropanol with isopropanolic hydrochloric acid.

Yield: 27% of theory; m.p. 235° C. (decomp.).

EXAMPLE 111

2-Acetyl-2,3,4,5-tetrahydro-11-methyl-1H-azepino[4,3-b]quinoline-6-oxide 6 gm (23.8 millimols) of 2-acetyl-2,3,4,5-tetrahydro-11-methyl-1H-azepino[4,3-b]quinoline were dissolved in 7 ml of glacial acetic acid, and 4 ml of 30% hydrogen peroxide were added to the solution at room temperature. The mixture was subsequently heated at 60° to 80° C. for 2 hours. After distilling off the solvent, the mixture was dissolved in 2 N sodium hydroxide, the resulting solution was extracted with chloroform, the solvent was distilled out of the chloroform extract, and the residue was recrystallized from ethyl acetate.

Yield: 83% of theory; m.p. 168° C.

EXAMPLE 112

1,2,4,5-Tetrahydro-11-methyl-3-azepino[4,5-b]quinoline-carboxylic acid ethyl ester 6-oxide was prepared analogous to Example 111 from 1,2,4,5-tetrahydro-11-methyl-3-azepino[4,5-b]quinoline-carboxylic acid ethyl ester and hydrogen peroxide.

Yield: 66% of theory; m.p. 164° C.

EXAMPLE 113

3-Acetyl-1,2,4,5-tetrahydro-11-methyl-3H-azepino[4,5-b]quinoline 6-oxide was prepared analogous to Example 111 from 3-acetyl-1,2,4,5-tetrahydro-11-methyl-3H-azepino[4,5-b]quinoline and hydrogen peroxide.

Yield: 83.5% of theory; m.p. 128° C.

EXAMPLE 114

1,2,4,5-Tetrahydro-11-methyl-3H-azepino[4,5-b]quinoline-6-oxide dihydrochloride was prepared from the corresponding 3-acetyl or 3-carboxylic acid ethyl ester compound by hydrolysis with 2 N hydrochloric acid at the boiling point.

Yield: 82% of theory; m.p. 249° C. (decomp.); m.p. of the base: 189° C.

EXAMPLE 115

2,3,4,5-Tetrahydro-11-methyl-1H-2-azepino[4,3-b]quinoline-carboxylic acid ethyl ester 6-oxide was prepared analogous to Example 111 from 2,3,4,5-tetrahydro-11-methyl-1H-2-azepino[4,3-b]quinoline-carboxylic acid ethyl ester and hydrogen peroxide.

Yield: 60% of theory; m.p. 129° C.

EXAMPLE 116

2,3,4,5-Tetrahydro-11-methyl-1H-azepino[4,3-b]quinoline-6-oxide dihydrochloride was prepared from the corresponding 2-acetyl compound by hydrolysis with 2 N hydrochloric acid at the boiling point.

Yield: 91% of theory; m.p. 236° C. (decomp.).

EXAMPLE 117

5-(Ethoxy-carbonyloxy)-1,2,4,5-tetrahydro-11-methyl-3-azepino[4,5-b]quinoline-carboxylic acid ethyl ester by method B 1.7 gm (6.95 millimols) of 1,2,4,5-tetrahydro-11-methyl-3-azepino[4,5-b]quinoline-carboxylic acid ethyl ester 6-oxide were dissolved in 40 ml of warm benzene, and then a solution of 1.83 ml (13.9 millimols) of triethylamine in 10 ml of benzene and a solution of 1.32 ml (b 13.9 millimols) of ethyl chloroformate in 10 ml of benzene were simultaneously added dropwise. The resulting mixture was heated at its boiling point for two hours, then filtered, the benzene was distilled off, and the residue was crystallized from ether.

Yield: 63% of theory; m.p. 128° C.

EXAMPLE 118

5-(Ethoxy-carbonyloxy)-2,3,4,5-tetrahydro-11-methyl-1H-2-azepino[4,3-b]quinoline-carboxylic acid ethyl ester was prepared analogous to Example 117 from 2,3,4,5-tetrahydro-11-methyl-1H-2-azepino[4,3-b]quinoline-carboxylic acid ethyl ester 6-oxide.

Yield: 50% of theory; m.p. 40° C.

EXAMPLE 119

2-Acetyl-5-acetoxy-2,3,4,5-tetrahydro-11-methyl-1H-azepino[4,3-b]quinoline by method B A mixture of 3 gm (11 millimols) of 2-acetyl-2,3,4,5-tetrahydro-11-methyl-1H-azepino[4,3-b]quinoline 6-oxide, 80 ml of benzene and 23 ml of acetic acid anhydride was heated at its boiling point for 3 hours. Thereafter, the benzene was distilled off and the residue was recrystallized from ether.

Yield: 70% of theory; m.p. 40° C.

EXAMPLE 120

1,2,4,5-Tetrahydro-5-hydroxy-11-methyl-3H-azepino[4,5-b]quinoline dihydrochloride was prepared from 5-(ethoxycarbonyloxy)-1,2,4,5-tetrahydro-11-methyl-3-azepino[4,5-b]quinoline-carboxylic acid ethyl ester by hydrolysis with 2 N hydrochloric acid for 36 hours at the boiling point. After distilling off the hydrochloric acid, the remaining water was removed by entrainment with benzene, and the raw salt was recrystallized from methanol.

Yield: 68% of theory; m.p. 255° C. (decomp.).

EXAMPLE 121

2,3,4,5-Tetrahydro-5-hydroxy-11-methyl-1H-azepino[4,3-b]quinoline dihydrochloride was prepared from 5-(ethoxy-carbonyloxy)-2,3,4,5-tetrahydro-11-methyl-1H-2-azepino[4,3-b]quinoline-carboxylic acid ethyl ester by hydrolysis with 2 N hydrochloric acid.

Yield: 70% of theory; m.p. 240° C. (decomp.).

EXAMPLE 122

3-Hydroxyethyl-1,2,4,5-tetrahydro-11-methyl-3H-azepino[4,5-b]quinoline dihydrochloride 4.24 gm (20 millimols) of. 1,2,4,5-tetrahydro-11-methyl-3H-azepino[4,5b]quinoline in 30 ml of methyl ethyl ketone were admixed with 3.68 gm (80 millimols) of ethylene oxide, and the resulting mixture was heated at 110° C. in an autoclave for 6 hours. After distilling off the solvent, the residue was dissolved in dilute hydrochloric acid, the resulting solution was extracted with chloroform, and the aqueous phase was made alkaline with sodium hydroxide and again extracted with chloroform. After drying the combined chloroform extracts and distilling off the chloroform, the dihydrochloride was obtained by dissolving the residue in ethanol and adding isopropanolic hydrochloric acid to the solution.

Yield: 33% of theory; m.p. 252° C. (decomp.).

EXAMPLE 123

1,2,4,5-Tetrahydro-3-(β-hydroxy-propyl)-11-methyl-3H-azepino[4,5-b]quinoline dihydrochloride was prepared analogous to Example 122 from 1,2,4,5-tetrahydro-11-methyl-3H-azepino[4,5-b]quinoline and propylene oxide.

Yield: 58% of theory; m.p. 273° C.

EXAMPLE 124

2-Hydroxyethyl-2,3,4,5-tetrahydro-11-methyl-1H-azepino[4,3-b]quinoline dihydrochloride was prepared analogous to Example 122 from 2,3,4,5-tetrahydro-11-methyl-1H-azepino[4,3-b]quinoline and ethylene oxide.

Yield: 24% of theory; m.p. 268° C. (decomp.).

EXAMPLE 125

2,3,4,5-Tetrahydro-2-(β-hydroxy-propyl)-11-methyl-1H-azepino[4,3-b]quinoline dihydrochloride was prepared analogous to Example 122 from 2,3,4,5-tetrahydro-11-methyl-1H-azepino[4,3-b]quinoline and propylene oxide.

Yield: 28% of theory; m. p. 268° C.

EXAMPLE 126

1,2,4,5-Tetrahydro-11-methyl-3-azepino[4,5-b]quinoline-carboxylic acid tert.butyl ester hydrochloride was prepared analogous to Example 63 with tert.butyl chloroformate.

Yield: 61% of theory; m.p. 212° C (decomp.).

EXAMPLE 127

1,2,4,5-Tetrahydro-9,11-dimethyl-3H-azepino[4,5-b]quinoline, 2,3,4,5-tetrahydro-9,11-dimethyl-1H-azepino[4,3-b]quinoline and their dihydrochloride by method A A mixture consisting of 6.6 gm (44.4 millimols) of hexahydroazepinone-(4) hydrochloride, 50 ml of 2 N hydrochloric acid and 6.6 gm of 2-amino-5-methyl-acetophenone was heated at its boiling point for 72 hours. Thereafter, the cooled reaction solution was made alkaline with concentrated sodium hydroxide and was then extracted with chloroform. After drying the chloroform extract over sodium sulfate and distilling off the solvent, a mixture of the [4,5-b]- and [4,3-b]isomers was obtained (ratio 2:3).

To separate the isomers, the mixture was dissolved in 15 ml of methanol and chromatographed on a silicagel column (diameter: 3 to 4 cm; height: 120 to 140 cm; grain size: 0.05 to 0.2 mm) with methanol as the eluant. The course of the column chromatography was monitored by thin-layer chromatography. The fractions containing only one of the respective isomers were combined, and the methanol was distilled out of each solution, leaving respectively 2.7 gm (27% of theory) of the [4,5-b]isomer, m.p. 68°–70° C, and 4.2 gm (42% of theory) of the [4,3-b]isomer, m.p. 150° C. For conversion into the dihydrochlorides, the bases were each dissolved in hot acetone, and isopropanolic hydrochloric acid was added. Upon cooling, the dihydrochlorides crystallized out. M.p. of the dihydrochloride of the [4,5-b]isomer: 300° C (decomp.). M.p. of the dihydrochloride of the [4,3-b]isomer: 293°–295° C (decomp.).

EXAMPLE 128

1,2,4,5-Tetrahydro-11-methyl-3-phenyl-3H-azepino[4,5-b]quinoline, 2,3,4,5-tetrahydro-11-methyl-2-phenyl-1H-azepino[4,3-b]quinoline and their dihydrochlorides by method A A solution of 2.7 gm (14.3 millimols) of 1-phenylhexahydro-azepinone-(4) and 1.95 gm (14.3 millimols) of 2-amino-acetophenone in 30 gm of polyphosphoric acid was heated at 120° to 140° C for 4 hours. After cooling, the reaction mixture was made alkaline with sodium hydroxide and the isomeric mixture of the raw bases was extracted with ether. After drying the ethereal extract over sodium sulfate and evaporating the solvent, 4 gm of a mixture of the [4,5-b]- and [4,3-b]isomers was obtained as a reddish oil.

The separation of the isomers was carried out analogous to Example 127, using benzene/ether (7:3) as the eluant.

Yield of the [4,5-b]isomer: 0.4 gm (10% of theory). M.p. of the dihydrochloride: 239° C. Yield of the [4,3-b]isomer: 0.4 gm (10% of theory). M.p. of the dihydrochloride: 196° C.

EXAMPLE 129

3-Allyl-1,2,4,5-tetrahydro-11-methyl-3H-azepino[4,5-b]quinoline, 2-allyl-2,3,4,5-tetrahydro-11-methyl-1H-azepino[4,3-b]quinoline and their dihydrochlorides by method A A mixture consisting of 5 gm (27.6 millimols) of 1-allyl-4-ethoxy-2,3,6,7-tetrahydro-azepine, 100 ml of toluene, 5,3 gm of p-toluenesulfonic acid and 3.75 gm (27.6 millimols) of 2-amino-acetophenone was heated at its boiling point for 2 hours in a vessel equipped with a water trap. Thereafter, the toluene was decanted from the precipitated p-toluenesulfonate salts, made alkaline and extracted with chloroform. After drying of the chloroform extract over sodium sulfate and distilling off the solvent, 6,5 gm of a mixture of the [4,5-b]- and [4,3-b]isomers were obtained.

For separation of the isomers, the mixture was dissolved in 50 ml of methanol and chromatographed on a silicagel column (diameter: 3 cm; height: 120 cm; grain size: 0.05 to 0.2 mm) with methanol as the eluant. The course of the column chromatography was thin-layer chromatographically monitored.

The fractions containing only one of the respective isomers were combined and the solvent was distilled out of each, leaving 0.2 gm (3% of theory) of the [4,5-b]isomer and 1.4 gm (20% of theory) of the [4,3-b]isomer as colorless oils.

For conversion into the dihydrochlorides the isomeric bases were each dissolved in hot isopropanol, and isopropanolic hydrochloric acid was added. Upon cooling, the dihydrochlorides crystallized out. M.p. of the dihydrochloride of the [4,5-b]isomer: 278° C. M.p. of the dihydrochloride of the [4,3-b]isomer: 270° C.

EXAMPLE 130

1,2,4,5-Tetrahydro-3-(2-methoxy-ethyl)-11-methyl-3H-azepino]4,5-b]quinoline and its dihydrochloride A warm solution of 1,2,4,5-tetrahydro-3-(2-methoxy-acetyl)-11-methyl-3H-azepino[4,5-b]quinoline in 60 ml of tetrahydrofuran was added dropwise to a suspension of 1.9 gm (50 millimols) of lithium aluminum hydride in 10 ml of absolute tetrahydrofuran, and the resulting mixture was stirred for 30 minutes. Thereafter, the excess lithium aluminum hydride was destroyed by adding 6 ml of ethyl acetate, and then 6 ml of water were added and the precipitated aluminum hydroxide was suction-filtered off and washed with chloroform. After drying the filtrate over sodium sulfate it was evaporated, the residue was dissolved in hot isopropylalcohol, and the dihydrochloride was precipitated by adding isopropanolic hydrochloric acid.

Yield: 4.9 gm (87% of theory); m.p. 250° C.

EXAMPLE 131

3-n-Hexyl-1,2,4,5-tetrahydro-11-methyl-3H-azepino[4,5-b]quinoline dihydrochloride was prepared from 3-caproyl-1,2,4,5-tetrahydro-11-methyl-3H-azepino[4,5-b]quinoline and lithium aluminum hydride analogous to Example 130.

Yield: 83% of theory; m.p. 240° C.

EXAMPLE 132

3-n-Butyl-1,2,4,5-tetrahydro-11-methyl-3H-azepino[4,5-b]quinoline dihydrochloride was prepared from 3-butyryl-1,2,4,5-tetrahydro-11-methyl-3H-azepino[4,5-b]quinoline and lithium aluminum hydride analogous to Example 130.

Yield: 85% of theory; m.p. 278° C.

EXAMPLE 133

1,2,4,5-Tetrahydro-8,11-dimethyl-3H-azepino[4,5-b]quinoline, 2,3,4,5-tetrahydro-8,11-dimethyl-1H-azepino[4,5-b]quinoline and their dihydrochlorides were prepared from hexahydro-azepinone-(4) hydrochloride and 2-amino-4-methyl-acetophenone analogous to Example 127. Yield of the dihydrochloride of the [4,5-b]-isomer: 17% of theory; m.p. 290°–292° C. (decomp.).

Yield of the dihydrochloride of the [4,3-b]-isomer: 32% of theory; m.p. 305°–307° C (decomp.).

EXAMPLE 134

8-Chloro-1,2,4,5-tetrahydro-11-methyl-3H-azepino[4,5-b]quinoline, 8-chloro-2,3,4,5-tetrahydro-11-methyl-1H-azepino[4,3-b]quinoline and their dihydrochlorides were prepared from hexahydro-azepinone-(4) hydrochloride and 2-amino-4-chloro-acetophenone analogous to Example 127.

Yield of the dihydrochloride of the [4,5-b]-isomer: 24% of theory; m.p. 287° C (decomp.).

Yield of the dihydrochloride of the [4,3-b]-isomer: 16% of theory; m.p. 304° C.

EXAMPLE 135

9-Fluoro-1,2,4,5-tetrahydro-11-methyl-3H-azepino[4,5-b]quinoline, 9-fluoro-2,3,4,5-tetrahydro-11-methyl-1H-azepino[4,3-b]quinoline and their dihydrochlorides were prepared from hexahydro-azepinone-(4) hydrochloride and 2-amino-5-fluoro-acetophenone analogous to Example 127.

Yield of the dihydrochloride of the [4,5-b]-isomer: 18% of theory; m.p. 278° C (decomp.). Yield of the dihydrochloride of the [4,3-b]-isomer: 24% of theory; m.p. 285° C (decomp.).

EXAMPLE 136

8,9-Dimethoxy-1,2,4,5-tetrahydro-11-methyl-3-azepino[4,5-b]quinoline-carboxylic acid ethyl ester, 8,9-dimethoxy-2,3,4,5-tetrahydro-11-methyl-1H-2-azepino[4,3-b]quinoline-carboxylic acid ethyl ester and their hydrochlorides were prepared from 1-ethoxycarbonyl-hexahydroazepinone-(4) and 2-amino-4,5-dimethoxy-acetophenone analogous to Example 129, except that ethyl acetate/methanol (95:5) was used as the eluant for the column chromatography.

Yield of the hydrochloride of the [4,5-b]-isomer: 15% of theory; m.p. 246° C (decomp.). Yield of the hydrochloride of the [4,3-b]-isomer: 22% of theory; m.p. 202° C (decomp.).

EXAMPLE 137

8,9-Dihydroxy-1,2,4,5-tetrahydro-11-methyl-3H-azepino]4,5-b]quinoline dihydrochloride was prepared from 8,9-dimethoxy-1,2,4,5-tetrahydro-11-methyl-3-azepino[4,5-b]quinoline-carboxylic acid ethyl ester by boiling it for 6 hours with 40% hydrobromic acid in glacial acetic acid. After distilling off the solvent, the residue was recrystallized from concentrated hydrochloric acid. Yield: 90% of theory; m.p. >330° C (decomp.).

EXAMPLE 138

8-Hydroxy-1,2,4,5-tetrahydro-11-methyl-9-methoxy-3H-azepino]4,5-b]quinoline,
8-hydroxy-2,3,4,5-tetrahydro-11-methyl-9-methoxy-1H-azepino [4,5-b]quinoline and their dihydrochlorides were prepared from hexahydroazepinone-(4) hydrochloride and 2-amino-4,5-dimethoxy-acetophenone analogous to Example 127.

Yield of the dihydrochloride of the [4,5-b]-isomer: 5% of theory; m.p. 325° C (decomp.). Yield of the dihydrochloride of the [4,3-b]-isomer: 4% of theory; m.p. 294° C (decomp.).

EXAMPLE 139

1,2,4,5-Tetrahydro-8,9-methylenedioxy-11-methyl-3H-azepino [4,5-b]quinoline, 2,3,4,5-tetrahydro-8,9-methylenedioxy-11-methyl-1H-azepino [4,5-b]quinoline and their dihydrochlorides were prepared from hexahydro-azepinone-(4) hydrochloride and 2-amino-4,5-methylenedioxy-acetophenone analogous to Example 127.

Yield of the dihydrochloride of the [4,5-b]-isomer: 8% of theory; m.p. > 300° C (decomp.). Yield of the dihydrochloride of the [4,3-b]-isomer: 10% of theory; m.p. > 300° C (decomp.).

EXAMPLE 140

9-Cyano-1,2,4,5-tetrahydro-11-methyl-3-azepino[4,5-b]quinoline-carboxylic acid ethyl ester and its hydrochloride A solution of 3.6 gm (12 millimols) of 9-amino-1,2,4,5-tetrahydro-11-methyl-3-azepino[4,5-b]quinoline-carboxylic acid ethyl ester in 3 ml of concentrated hydrochloric acid and 20 ml of water was diazotized with a solution of 0.84 gm (12.2 millimols) of sodium nitrite in 3 ml of water at 0° C, and subsequently the reaction mixture was neutralized with the equimolar quantity of sodium carbonate. The resulting solution was added dropwise to an aqueous solution of complex copper-I-cyanide (15 millimols). After heating for 2 hours at 50°–60° C the mixture was cooled, and the base was extracted with chloroform. Yield: 35% of theory; m.p. 182° C. The hydrochloride, prepared in acetone with isopropanolic hydrochloric acid, melted at 217° C.

EXAMPLE 141

7-Cyano-1,2,4,5-tetrahydro-11-methyl-3-azepino[4,5-b]quinoline-carboxylic acid ethyl ester hydrochloride was prepared from 7-amino-1,2,4,5-tetrahydro-11-methyl-3-azepino[4,5-b]quinoline-carboxylic acid ethyl ester analogous to Example 140.

Yield: 42% of theory; m.p. 208° C.

EXAMPLE 142

9-Acetyl-1,2,4,5-tetrahydro-11-methyl-3-azepino[4,5-b]quinoline-carboxylic acid ethyl ester hydrochloride A solution of 2 gm (6.5 millimols) of 9-cyano-1,2,4,5-tetrahydro-11-methyl-3-azepino[4,5-b]quinoline-carboxylic acid ethyl ester in 50 ml of absolute tetrahydrofuran was added dropwise to a Grignard solution prepared from 0.4 gm of magnesium and 2.3 gm (16.4 millimols) of methyl iodide in 20 ml of ether, and the resulting mixture was heated at its boiling point for 6 hours. After cooling, the mixture was acidified with 20 ml of semi-concentrated hydrochloric acid, and the aqueous phase was separated and heated at its boiling point for 1 hour. Thereafter, it was saturated with ammonium chloride, and the resulting mixture was made alkaline with sodium carbonate and was then extracted with chloroform. Evaporation of the chloroform extract left the base as a residue.

Yield: 20% of theory; m.p. 155° C. M.p. of its hydrochloride: 212° C (decomp.).

EXAMPLE 143

3-Acetyl-9-cyano-1,2,4,5-tetrahydro-11-methyl-3H-azepino[4,5-b]quinoline hydrochloride was prepared from 3-acetyl-9-amino-1,2,4,5-tetrahydro-11-methyl-3H-azepino[4,5-b]quinoline analogous to Example 140.

Yield: 28% of theory; m.p. 245° C.

EXAMPLE 144

1,2,4,5-Tetrahydro-11-methyl-3H-azepino[4,5-b]quinoline-9-carboxylic acid dihydrochloride was prepared by acid hydrolysis of 3-acetyl-9-cyano-1,2,4,5-tetrahydro-3H-azepino[4,5-b]quinoline.

Yield: 75% of theory; m.p. 300° C (decomp.).

EXAMPLE 145

1,2,4,5-Tetrahydro-11-methyl-3H-azepino[4,5-b]quinoline-9-carboxylic acid ethyl ester dihydrochloride was prepared from 1,2,4,5-tetrahydro-11-methyl-3H-azepino[4,5-b]quinoline-9-carboxylic acid by esterification with ethanolic hydrochloric acid.

Yield: 90% of theory; m.p. 250° C (decomp.).

EXAMPLE 146

2-Acetyl-9-cyano-2,3,4,5-tetrahydro-11-methyl-1H-azepino[4,3-b]quinoline hydrochloride was prepared from 2-acetyl-9-amino-2,3,4,5-tetrahydro-1H-azepino[4,3-b]quinoline analogous to Example 140.

Yield: 36% of theory; m.p. 230° C (decomp.).

EXAMPLE 147

2,3,4,5-Tetrahydro-11-methyl-1H-azepino[4,3-b]quinoline-9-carboxylic acid dihydrochloride was prepared by acid hydrolysis of 2-acetyl-9-cyano-2,3,4,5-tetrahydro-11-methyl-1H-azepino[4,3-b]quinoline.

Yield: 80% of theory; m.p. 305° C (decomp.).

EXAMPLE 148

2-Acetyl-10-bromo-9-hydroxy-2,3,4,5-tetrahydro-11-methyl-1H-azepino[4,3-b]quinoline 2.5 gm (9.3 millimols) of 2-acetyl-9-hydroxy-2,3,4,5-tetrahydro-11-methyl-1H-azepino[4,3-b]quinoline were dissolved in 60 ml of glacial acetic acid and 12 ml of water, and the solution was brominated at room temperature with a solution of 1.48 gm (9.3 millimols) of bromine in 10 ml of glacial acetic acid. After distilling off the solvent, the residue was dissolved in water, and the solution was adjusted to a pH-value of 7.5 with 2 N sodium hydroxide, whereupon the reaction product crystallized out.

Yield: 62% of theory; m.p. 190° C (decomp.).

EXAMPLE 149

10-Bromo-9-hydroxy-2,3,4,5-tetrahydro-11-methyl-1H-azepino[4,3-b]quinoline hydrochloride was prepared by acid hydrolysis of 2-acetyl-10-bromo-9-hydroxy-2,3,4,5-tetrahydro-11-methyl-1H-azepino[4,3-b]quinoline.

Yield: 80% of theory; m.p. > 300° C (decomp.).

EXAMPLE 150

8,10-Dibromo-7-hydroxy-2,3,4,5-tetrahydro-11-methyl-1H-azepino[4,3-b]quinoline dihydrochloride was prepared from 7-hydroxy-2,3,4,5-tetrahydro-11-methyl-1H-azepino[4,3-b]quinoline by bromination with two molar equivalents of bromine analogous to Example 148.

Yield: 22% of theory; m.p. > 300° C (decomp.).

EXAMPLE 151

9-Amino-10-bromo-2,3,4,5-tetrahydro-11-methyl-1H-azepino[4,3-b]quinoline dihydrochloride was prepared from 9-amino-2,3,4,5-tetrahydro-11-methyl-1H-azepino[4,3-b]quinoline dihydrochloride by bromination with an equimolar quantity of bromine analogous to Example 148.

Yield: 60% of theory; m.p. 312° C (decomp.).

EXAMPLE 152

9-Amino-10-bromo-1,2,4,5-tetrahydro-11-methyl-3H-azepino[4,5-b]quinoline dihydrochloride was prepared from 9-amino-1,2,4,5-tetrahydro-11-methyl-3H-azepino[4,5-b]quinoline dihydrochloride by bromination with an equimolar quantity of bromine analogous to Example 148.

EXAMPLE 153

8,10-Dibromo-7-hydroxy-1,2,4,5-tetrahydro-11-methyl-3-azepino[4,5-b]quinoline-carboxylic acid ethyl ester was prepared from 7-hydroxy-1,2,4,5-tetrahydro-11-methyl-3-azepino[4,5-b]quinoline-carboxylic acid ethyl ester by bromination with two molar equivalents of bromine analogous to Example 148.

Yield: 36% of theory; m.p. 179° C.

EXAMPLE 154

9-Amino-1,2,4,5-tetrahydro-11-methyl-3-azepino[4,5-b]quinoline-carboxylic acid ethyl ester was prepared from 9-nitro-1,2,4,5-tetrahydro-11-methyl-3-azepino[4,5-b]quinoline-carboxylic acid ethyl ester by reduction with nascent hydrogen, generated in situ by concentrated hydrochloric acid and tin(II)chloride, at a temperature of 60°–80° C.

Yield: 95% of theory; m.p. 214°–216° C.

EXAMPLE 155

9.11-Dimethyl-1,2,4,5-tetrahydro-3-azepino[4,5-b]quinoline-carboxylic acid ethyl ester hydrochloride 1.1 gm (5 millimols) of 9,11-dimethyl-1,2,4,5-tetrahydro-3H-azepino[4,5-b]quinoline were dissolved in 30 ml of benzene, and a solution of 1 gm (10 millimols) of triethylamine in 10 ml of benzene and then 1.08 gm (10 millimols) of ethyl chloroformate were added, and the resulting mixture was heated at its boiling point for 2 hours. The cooled reaction mixture was admixed with 50 ml of ice water, and the aqueous mixture was made alkaline with 2 N sodium hydroxide. The benzene phase was separated, and the aqueous layer was extracted with chloroform. The benzene phase and the chloroform extract were combined, dried over sodium sulfate, and the solvents were distilled off. For conversion into the hydrochloride, the residual base was dissolved in hot acetone, and the solution was acidified with isopropanolic hydrochloric acid, whereupon the hydrochloride crystallized out.

Yield: 85% of theory; m.p. 212° C (decomp.).

EXAMPLE 156

8-Chloro-1,2,4,5-tetrahydro-11-methyl-3-azepino[4,5-b]quinoline-carboxylic acid ethyl ester hydrochloride was prepared from 8-chloro-1,2,4,5-tetrahydro-11-methyl-3H-azepino[4,5-b]quinoline and ethyl chloroformate analogous to Example 155.

Yield: 70% of theory; m.p. 230° C.

EXAMPLE 157

1,2,4,5-Tetrahydro-10-hydroxy-11-methyl-3-azepino[4,5-b]quinoline-carboxylic acid ethyl ester hydrochloride A solution of 6 gm (20 millimols) of 10-amino-1,2,4,5-tetrahydro-11-methyl-3-azepino[4,5-b]quinoline-carboxylic acid ethyl ester in 66 ml of water and 9 ml of concentrated sulfuric acid was diazotized at 0° C with 1.53 gm (22 millimols) of sodium nitrite. The reaction solution was then added to a mixture of 21 ml of water and 27 ml of concentrated sulfuric acid at 100° C, whereby the desired compound crystallized out, accompanied by evolution of nitrogen. The compound was dissolved in 2 N sodium hydroxide, the solution was filtered, and the hydrochloride was caused to crystallize out by acidification of the filtrate with hydrochloric acid.

Yield: 29% of theory; m.p. 303° C.

EXAMPLE 158

10-Chloro-1,2,4,5-tetrahydro-11-methyl-3-azepino[4,5-b]quinoline-carboxylic acid ethyl ester was prepared from 10-amino-1,2,4,5-tetrahydro-11-methyl-3-azepino[4,5-b]quinoline-carboxylic acid ethyl ester by the Sandmeyer Reaction with copper-I-chloride analogous to Example 140.

Yield: 37% of theory; m.p. 138° C.

EXAMPLE 159

8,11-Dimethyl-2,3,4,5-tetrahydro-1H-2-azepino[4,3-b]quinoline-carboxylic acid ethyl ester was prepared from 8,11-dimethyl-2,3,4,5-tetrahydro-1H-azepino[4,3-b]quinoline and ethyl chloroformate analogous to Example 155.

Yield: 42% of theory; m.p. 132° C.

EXAMPLE 160

1,2,4,5-Tetrahydro-11-carboxyl-3-azepino[4,5-b]quinoline-carboxylic acid ethyl ester was prepared from 1,2,4,5-tetrahydro-3H-azepino[4,5-b]quinoline-11-carboxylic acid and ethyl chloroformate analogous to Example 155.

Yield: 57% of theory; m.p. 247° C.

EXAMPLE 161

1,2,4,5-Tetrahydro-3H-azepino[4,5-b]quinoline-3,11-dicarboxylic acid diethyl ester was prepared by alcoholysis of 1,2,4,5-tetrahydro-3-azepino[4,5-b]quinoline-carboxylic acid ethyl ester-11-(carboxylic acid-carbonic acid-ethyl ester anhydride).

Yield: 10% of theory; m.p. 94° C.

EXAMPLE 162

1,2,4,5-Tetrahydro-11-hydroxymethyl-3-azepino[4,5-b]quinoline-carboxylic acid ethyl ester was prepared from 1,2,4,5-tetrahydro-3-azepino[4,5-b]quinoline-carboxylic acid ethyl ester-11-carboxylic acid by reduction with lithium aluminum hydride in tetrahydrofuran at room temperature.

Yield: 12% of theory; m.p. 158° C.

EXAMPLE 163

1,2,4,5-Tetrahydro-3-azepino[4,5-b]quinoline-carboxylic acid ethyl ester-11-carboxylic acid-6-oxide 7 gm (22 millimols) of 1,2,4,5-tetrahydro-3-azepino[4,5-b]quinoline-carboxylic acid ethyl ester-11-carboxylic acid were suspended in 7 ml of glacial acetic acid, the suspension was admixed with 7 ml of 30% hydrogen peroxide, and the resulting mixture was heated at 70° C for 16 hours. After distilling off the solvent, the residue was dissolved in water, and the aqueous solution was extracted with chloroform. The chloroform phase was dried over sodium sulfate and evaporated, and the residue was recrystallized from ethyl acetate.

Yield: 2.7 gm (37% of theory); m.p. 202° C (decomp.).

EXAMPLE 164

5-Acetoxy-1,2,4,5-tetrahydro-11-methyl-3-azepino[4,5-b]quinoline-carboxylic acid ethyl ester-6-oxide was prepared from 5-acetoxy-1,2,4,5-tetrahydro-11-methyl-3-azepino[4,5-b]quinoline-carboxylic acid ethyl ester analogous to Example 163.

Yield: 23% of theory; m.p. 130° C.

EXAMPLE 165

5-Hydroxy-1,2,4,5-tetrahydro-11-methyl-3-azepino[4,5-b]quinoline-carboxylic acid ethyl ester-6-oxide was prepared from 5-hydroxy-1,2,4,5-tetrahydro-11-methyl-3-azepino[4,5-b]quinoline-carboxylic acid ethyl ester and hydrogen peroxide analogous to Example 163.

Yield: 17% of theory; m.p. 199° C.

EXAMPLE 166

5-Hydroxy-1,2,4,5-tetrahydro-3-azepino[4,5-b]quinoline-carboxylic acid ethyl ester-11-carboxylic acid was prepared from 1,2,4,5-tetrahydro-3-azepino[4,5-b]quinoline-carboxylic acid ethyl ester-11-carboxylic acid-6N-oxide and acetic acid anhydride in benzene and subsequent hydrolysis of the 2-acetoxy-intermediate.

Yield: 1% of theory; m.p. > 300° C (decomp.)

EXAMPLE 167

5-Hydroxy-1,2,4,5-tetrahydro-11-hydroxymethyl-3-azepino[4,5-b]quinoline-carboxylic acid ethyl ester A mixture of 1.5 gm (4.75 millimols) of 5-hydroxy-1,2,4,5-tetrahydro-11-methyl-3-azepino[4,5-b]quinoline-carboxylic acid ethyl ester-6N-oxide and 50 ml of acetic acid anhydride was heated at 110° C for 2 hours. After distilling off the acetic acid anhydride and the acetic acid, the residue was refluxed for 30 minutes with 2 N hydrochloric acid. Subsequently, the reaction mixture was made alkaline with 2 N sodium hydroxide, extracted with chloroform, and the evaporation residue of the chloroform extract was purified on a silicagel column with ethyl acetate as the eluant.

Yield: 0.4 gm (35% of theory); m.p. 171° C.

EXAMPLE 168

5-Chloro-1,2,4,5-tetrahydro-11-methyl-3-azepino[4,5-b]quinoline-carboxylic acid ethyl ester 1 gm (3.3 millimols) of 5-hydroxy-1,2,4,5-tetrahydro-11methyl-3-azepino[4,5-b]quinoline-carboxylic acid ethyl ester was stirred for 2 hours with 20 ml of thionyl chloride at room temperature. The excess thionyl chloride was then distilled off in vacuo, the residue was dissolved in chloroform, the solution was dried with sodium sulfate, and the solvent was distilled off. After purification of the residue on a silicagel column with benzene/ethyl acetate (8:2) as the eluant, the yield was 0.55 gm (52% of theory), m.p. 131° C.

EXAMPLE 169

2-Acetyl-5-chloro-2,3,4,5-tetrahydro-11-methyl-1H-azepino[4,3-b]quinoline was prepared from 2-acetyl-5-hydroxy-2,3,4,5-tetrahydro-11-methyl-1H-azepino[4,3-b]quinoline analogous to Example 168.

Yield: 77% of theory; m.p. < 20° C.

EXAMPLE 170

5-Methoxy-1,2,4,5-tetrahydro-11-methyl-3-azepino[4,5-b]quinoline-carboxylic acid ethyl ester 2 gm (6.65 millimols) of 5-hydroxy-1,2,4,5-tetrahydro-11-methyl-3-azepino[4,5-b]quinoline-carboxylic acid ethyl ester were converted into the sodium salt in 50 ml of absolute tetrahydrofuran with 0.32 gm (7 millimols) of 50% sodium hydride, and the salt was methylated with 0.43 ml (7 millimols) of methyl iodide.

Yield: 1.3 gm (62% of theory) m.p. < 20° C.

EXAMPLE 171

1,2-Dihydro-11-methyl-3-azepino[4,5-b]quinoline-carboxylic acid ethyl ester hydrochloride was prepared from 1,2-dihydro-11-methyl-3H-azepino[4,5-b]quinoline and ethyl chloroformate analogous to Example 155.

Yield: 42% of theory; m.p. 218° C.

EXAMPLE 172

1,2-Dihydro-11-methyl-3H-azepino[4,5-b]quinoline

A mixture of 3 gm (5.42 millimols) of 5-chloro-1,2,4,5-tetrahydro-11-methyl-3-azepino[4,5-b]quinoline-carboxylic acid ethyl ester, 45 millimols of sodium ethoxide and 150 ml of ethanol was boiled for 2 hours. After distilling off the ethanol, the residue was dissolved in water, the solution was extracted with chloroform, the extract was dried with sodium sulfate, the solvent was evaporated, and the residue was recrystallized from ether.

Yield: 1.9 gm (95% of theory); m.p. 153° C (decomp.).

EXAMPLE 173

5-Amino-1,2,4,5-tetrahydro-11-methyl-3-azepino[4,5-b]quinoline-carboxylic acid ethyl ester and its dihydrochloride A mixture of 2 gm (6.3 millimols) of 5-chloro-1,2,4,5-tetrahydro-11-methyl-3-azepino[4,5-b]quinoline-carboxylic acid-ethyl ester and 15 ml of liquid ammonia was heated in an autoclave at 80° C for 4 hours. After evaporation of the excess ammonia, the residue was dissolved in ethyl acetate, and the solution was chromatographed on a silicagel column with ethyl acetate as the eluant. For conversion into the dihydrochloride, the base thus obtained was treated with isopropanolic hydrochloric acid.

Yield: 10% of theory; m.p. 236° C.

EXAMPLE 174

5-Dimethylamino-1,2,4,5-tetrahydro-11-methyl-3-azepino[4,5-b]quinoline-carboxylic acid ethyl ester dihydrochloride was prepared from 5-chloro-1,2,4,5-tetrahydro-11-methyl-3-azepino[4,5-b]quinoline-carboxylic acid ethyl ester and dimethylamine analogous to Example 173.

Yield: 77% of theory; m.p. 173° C.

EXAMPLE 175

5-Morpholino-1,2,4,5-tetrahydro-11-methyl-3-azepino[4,5-b]quinoline-carboxylic acid ethyl ester dihydrochloride was prepared from 5-chloro-1,2,4,5-tetrahydro-11-methyl-3-azepino[4,5-b]quinoline-carboxylic acid ethyl ester and morpholine analogous to Example 173, but at atmospheric pressure.

Yield: 51% of theory; m.p. 222° C (decomp.).

EXAMPLE 176

3-Butyryl-1,2,4,5-tetrahydro-11-methyl-3H-azepino[4,5-b]quinoline was prepared by acylation of 1,2,4,5-tetrahydro-11-methyl-3H-azepino[4,5-b]quinoline with butyric acid chloride in pyridine.

Yield: 67% of theory; m.p. 130° C.

EXAMPLE 177

3-Propionyl-1,2,4,5-tetrahydro-11-methyl-3H-azepino[4,5-b]quinoline was prepared by acylation of 1,2,4,5-tetrahydro-11-methyl-3H-azepino[4,5-b]quinoline with propionic acid chloride in pyridine.

Yield: 72% of theory; m.p. 128°–130° C.

EXAMPLE 178

3-Isobutyryl-1,2,4,5-tetrahydro-11-methyl-3H-azepino[4,5-b]quinoline was prepared by acylation of 1,2,4,5-tetrahydro-11-methyl-3H-azepino[4,5-b]quinoline with isobutyryl chloride in pryidine.

Yield: 50% of theory; m.p. 107° C.

EXAMPLE 179

3-Caproyl-1,2,4,5-tetrahydro-11-methyl-3H-azepino[4,5-b]quinoline was prepared by acylation of 1,2,4,5-tetrahydro-11-methyl-3H-azepino[4,5-b]quinoline with caproyl chloride in pyridine.

Yield: 82% of theory; m.p. 109° C.

EXAMPLE 180

3-Lauroyl-1,2,4,5-tetrahydro-11-methyl-3H-azepino[4,5-b]quinoline was prepared by acylation of 1,2,4,5-tetrahydro-11-methyl-3H-azepino[4,5-b]quinoline with lauroyl chloride in pyridine.

Yield: 86% of theory; m.p. 100° C.

EXAMPLE 181

3-(2-Methoxy-acetyl)-1,2,4,5-tetrahydro-11-methyl-3H-azepino[4,5-b]quinoline was prepared by acylation of 1,2,4,5-tetrahydro-11-methyl-3H-azepino[4,5-b]quinoline with 2-methoxy-acetic acid chloride in pyridine.

Yield: 79% of theory; m.p. 116° C.

EXAMPLE 182

3-Trifluoroacetyl-1,2,4,5-tetrahydro-11-methyl-3H-azepino[4,5-b]quinoline was prepared by acylation of 1,2,4,5-tetrahydro-11-methyl-azepino[4,5-b]quinoline with trifluoroacetic acid anhydride in benzene.

Yield: 66% of theory; m.p. 147° C.

EXAMPLE 183

3-Methylsulfonyl-1,2,4,5-tetrahydro-11-methyl3H-azepino[4,5-b]quinoline hydrochloride was prepared by acylation of 1,2,4,5-tetrahydro-11-methyl-azepino[4,5-b]quinoline with mesyl chloride in pyridine.

Yield: 73% of theory; m.p. 265° C.

EXAMPLE 184

3-p-Toluenesulfonyl-1,2,4,5-tetrahydro-11-methyl-3H-azepino[4,5-b]quinoline hydrochloride was prepared by acylation of 1,2,4,5-tetrahydro-11-methyl-3H-azepino[4,5-b]quinoline with -toluenesulfonyl chloride in pyridine.

Yield: 50% of theory; m.p. 236° C (decomp.).

EXAMPLE 185

3-(p-Chloro-benzene sulfonyl)-1,2,4,5-tetrahydro-11-methyl-3H-azepino[4,5-b]quinoline was prepared by acylation of 1,2,4,5-tetrahydro-11-methyl-3H-azepino[4,5-b]quinoline with 4-chlorobenzene sulfochloride in pyridine.

Yield: 75% of theory; m.p. 189° C.

EXAMPLE 186

2-[1,2,4,5-Tetrahydro-11-methyl-3H-azepino[4,5-b]quinoline-3-yl]acetic acid ethyl ester dihydrochloride 15 ml (141 millimols) of ethyl chloroacetate were added dropwise to a boiling solution of 30 gm (141 millimols) of 1,2,4,5-tetrahydro-11-methyl-3H-azepino[4,5-b]quinoline in 200 ml of benzene and 20 ml of triethylamine. After filtering off the precipitated triethylamine hydrochloride, the solvent was distilled off, and the residual base was converted into the dihydrochloride in ethanol with ethanolic hydrochloric acid.

Yield: 61% of theory; m.p. 225° C.

EXAMPLE 187

2-[1,2,4,5-Tetrahydro-11-methyl-3H-azepino[4,5-b]quinoline-3-yl]acetic acid dihydrochloride was prepared by hydrolysis of 2-[1,2,4,5-tetrahydro-11-methyl-3H-azepino[4,5-b]quinoline-3-yl]acetic acid ethyl ester in 2 N hydrochloric acid at the boiling point.

Yield: 72% of theory; m.p. 287° C (decomp.).

EXAMPLE 188

3-[1,2,4,5-Tetrahydro-11-methyl-3H-azepino[4,5-b]quinoline-3-yl]propionic acid ethyl ester dihydrochloride 5 gm (23.6 millimols) of 1,2,4,5-tetrahydro-11-methyl-3H-azepino[4,5-b]quinoline were dissolved in 100 ml of ethanol, and a solution of 2.6 ml (24.0 millimols) of ethyl acrylate in 20 ml of ethanol was added dropwise at room temperature. After heating the resulting mixture for 2 hours at its boiling point, most of the ethanol was distilled off, and the dihydrochloride was formed in situ by addition of ethanolic hydrochloric acid.

Yield: 72.5% of theory; m.p. 190° C.

EXAMPLE 189

3-[1,2,4,5-Tetrahydro-11-methyl-3H-azepino[4,5-b]quinoline-3-yl]propionic acid dihydrochloride was prepared by hydrolysis of 3-[1,2,4,5-tetrahydro-11-methyl-3H-azepino[4,5-b]quinoline-3-yl]propionic acid ethyl ester with 2 N hydrochloric acid at reflux temperature.

Yield: 76% of theory; m.p. 270° C (decomp.).

EXAMPLE 190

3-[1,2,4,5-Tetrahydro-11-methyl-3H-azepino[4,5-b]quinoline-3-yl]propionic acid morpholide dihydrochloride 3.3 gm (9.25 millimols) of 3-[1,2,4,5-tetrahydro-11-methyl-3H-azepino[4,5-b]quinoline-3yl]propionic acid were converted into the acid chloride with 50 ml of thionylchloride. After distilling off the excess thionyl chloride, the residue was dissolved in 100 ml of benzene, and the solution was heated at its boiling point with 3 ml (35 millimols) of morpholine for 3 hours. After filtering, the solvent was distilled off in vacuo. The residue was dissolved in 2 N sodium hydroxide, the solution was extracted with chloroform, and the chloroform phase was dried over sodium sulfate and evaporated. The evaporation residue was dissolved in hot isopropanol and acidified with isopropanolic hydrochloric acid. Upon cooling, the dihydrochloride crystallized out.

Yield: 43% of theory; m.p. 190° C (decomp.).

EXAMPLE 191

3-[1,2,4,5-Tetrahydro-11-methyl-3H-azepino[4,5-b]quinoline-3-yl]propionic acid dimethylamide dihydrochloride was prepared from 3-[1,2,4,5-tetrahydro-11-methyl-3H-azepino[4,5-b]quinoline-3-yl]propionic acid and dimethylamine analogous to Example 190.

Yield: 62% of theory; m.p. 264° C (decomp.).

EXAMPLE 192

2-[1,2,4,5-Tetrahydro-11-methyl-3H-azepino[4,5-b]quinoline-3-yl]acetonitrile dihydrochloride was prepared from 1,2,4,5-tetrahydro-11-methyl-3H-azepino[4,5-b]quinoline and chloroacetonitrile analogous to Example 186.

Yield: 25% of theory; m.p. 250° C.

EXAMPLE 193

3-[1,2,4,5-Tetrahydro-11-methyl-3H-azepino[4,5-b]quinoline-3-yl]propionitrile dihydrochloride was prepared from 1,2,4,5-tetrahydro-11-methyl-3H-azepino[4,5-b]quinoline and acrylonitrile analogous to Example 188.

Yield: 86% of theory; m.p. 266° C.

EXAMPLE 194

2-[1,2,4,5-Tetrahydro-11-methyl-3H-azepino[4,5-b]quinoline-3-yl]acetic acid dimethylamide dihydrochloride was prepared from 1,2,4,5-tetrahydro-11-methyl-3H-azepino[4,5-b]quinoline and chloroacetyl dimethylamide analogous to Example 186.

Yield: 68% of theory; m.p. 261° C (decomp.).

EXAMPLE 195

2-[1,2,4,5-Tetrahydro-11-methyl-3H-azepino[4,5-b]quinoline-3-yl]acetic acid morpholide dihydrochloride was prepared from 1,2,4,5-tetrahydro-11-methyl-3H-azepino[4,5-b]quinoline and chloroacetyl morpholide analogous to Example 186.

Yield: 59% of theory; m.p. 253° C (decomp.).

EXAMPLE 196

2-Acetyl-5-morpholino-2,3,4,5-tetrahydro-11-methyl-1H-azepino[4,5-b]quinoline was prepared from 2-acetyl-5-chloro-2,3,4,5-tetrahydro-11-methyl-1H-azepino[4,3-b]quinoline and morpholine analogous to Example 173, but at atmospheric pressure.

Yield: 13% of theory; m.p. 179° C.

EXAMPLE 197

1,2,4,5-Tetrahydro-11-hydroxymethyl-3-azepino[4,5-b]quinoline-carboxylic acid ethyl ester-6-oxide was prepared from 1,2,4,5-tetrahydro-11-hydroxymethyl-3-azepino4,5-b]quinoline-carboxylic acid ethyl ester and hydrogen peroxide analogous to Example 163.

Yield: 21% of theory; m.p. 207° C.

EXAMPLE 198

1,2,4,5-Tetrahydro-3H-azepino[4,5-b]quinoline-11-carboxylic acid-6-oxide hydrochloride was prepared from 1,2,4,5-tetrahydro-3-azepino[4,5-b]quinoline-carboxylic acid ethyl ester-11-carboxylic acid-6-oxide by hydrolysis with semi-concentrated hydrochloric acid at the boiling point.

Yield: 25% of theory; m.p. 240° C (decomp,).

EXAMPLE 199

1,2,4,5-Tetrahydro-11-methyl-8-trifluoromethyl-3H-azepino[4,5-b]quinoline, 2,3,4,5-tetrahydro-11-methyl-8-trifluoromethyl-1H-azepino[4,3-b]quinoline and their dihydrochlorides were prepared from 2-amino-4-trifluoromethyl-acetophenone and hexahydroazepinone -(4) hydrochloride analogous to Example 128.

Yield of the dihydrochloride of the [4,5-b]-isomer: 38.2% of theory; m.p. 275° C. Yield of the dihydrochloride of the [4,3-b]-isomer: 38.2% of theory; m.p. 270° C.

EXAMPLE 200

1,2,4,5-Tetrahydro-11-methyl-9-trifluoromethyl-3H-azepino[4,5-b]quinoline, 2,3,4,5-tetrahydro-11-methyl-9-trifluoromethyl-1H-azepino[4,3-b]quinoline and their dihydrochlorides were prepared from 2-amino-5-trifluoromethyl-acetophenone and hexahydroazepinone -(4) hydrochloride analogous to Example 128.

Yield of the dihydrochloride of the [4,5-b]-isomer: 24% of theory; m.p. 283° C. Yield of the dihydrochloride of the [4,3-b]-isomer: 23% of theory; m.p. 274° C.

EXAMPLE 201

1,2,4,5-Tetrahydro-11-methyl-8-trifluoromethyl-3-azepino[4,5-b]quinoline-carboxylic acid ethyl ester hydrochloride was prepared from 1,2,4,5-tetrahydro-11-methyl-8-trifluoromethyl-3H-azepino[4,5-b]quinoline and ethyl chloroformate analogous to Example 155.

Yield: 98% of theory; m.p. 142° C.

EXAMPLE 202

1,2,4,5-Tetrahydro-11-methyl-9-trifluoromethyl-3-azepino[4,5-b]quinoline-carboxylic acid ethyl ester hydrochloride was prepared from 1,2,4,5-tetrahydro-11-methyl-9-trifluoromethyl-3H-azepino[4,5-b]quinoline and ethyl chloroformate analogous to Example 155.

Yield: 90% of theory; m.p. 152° C.

EXAMPLE 203

11-Phenoxy-1,2,4,5-tetrahydro-3-azepino[4,5-b]quinoline-carboxylic acid ethyl ester A mixture of 15.0 gm (49.4 millimols) of 11-chloro-1,2,4,5-tetrahydro-3-azepino[4,5-b]quinoline-carboxylic acid ethyl ester and 28.2 gm (300 millimols) of phenol was melted at 150° C and held at that temperature for 40 hours. Then, the mixture was taken up in ethyl acetate, and the solution was extracted with dilute sodium hydroxide. The ethyl acetate phases were evaporated and chromatographed on a silicagel column with toluene/acetone (8:1) as the eluant. Subsequently, the crystals were triturated with ether/petroleum ether.

Yield: 58.2% of theory; m.p. 112° C.

EXAMPLE 204

2-Ethyl-11-morpholino-2,3,4,5-tetrahydro-1H-azepino[4,3-b]quinoline dihydrochloride A mixture of 3.0 gm (9 millimols) of 2-ethyl-11-chloro-2,3,4,5-tetrahydro-1H-azepino[4,3-b]quinoline dihydrochloride and 1.9 gm (20 millimols) of phenol heated at 120° C in a nitrogen gas atmosphere for 90 minutes. Then, 2.6 gm (30 millimols) of morpholine were added dropwise, and the mixture was stirred for 6 hours at 140° C and was then poured into dilute hydrochloric acid. After extraction with ethyl acetate, the aqueous phase was made alkaline and was extracted with chloroform. After evaporation of the chloroform extract, the dihydrochloride was precipitated from ethanol with isopropanolic hydrochloric acid.

Yield of the dihydrochloride: 31% of theory; m.p. 246° C (decomp.).

EXAMPLE 205

1,2,4,5-Tetrahydro-11-pyrrolidino-3-azepino[4,5-b]quinoline-carboxylic acid ethyl ester was prepared from 1,2,4,5-tetrahydro-11-chloro-3-azepino[4,5-b]quinoline-carboxylic acid ethyl ester and pyrrolidine analogous to Example 204.

Yield: 18% of theory; m.p. 111° C.

EXAMPLE 206

11-Amino-3-benzyl-1,2,4,5-tetrahydro-3H-azepino[4,5-b]quinoline and 11-amino-2-benzyl-2,3,4,5-tetrahydro-1H-azepino[4,3-b]quinoline by method A A mixture of 11.8 gm (100 millimols) of o-aminobenzonitrile, 24.0 gm (100 millimols) of 1-benzyl-hexahydroazepinone-(4) hydrochloride and 250 gm of polyphosphoric acid was stirred at 140° C for 1 hour. After decomposition with ice water, chloroform and sodium hydroxide were added, and the chloroform phase was evaporated. The residue was purified by column chromatography on silicagel with chloroform/methanol (3:1) as the eluant.

Yield of the [4,5-b]-isomer: 13% of theory; m.p. 138° C. Yield of the [4,3-b]-isomer: 13% of theory; m.p. 149° C.

EXAMPLE 207

3-Benzyl-11-methoxy-1,2,4,5-tetrahydro-3H-azepino[4,5-b] quinoline 19.9 gm (50 millimols) of 3-benzyl-11-chloro-1,2,4,5-tetrahydro-3H-azepino[4,5-b]quinoline dihydrochloride and 500 ml of dimethyl formamide were added to dry sodium methylate, prepared from 23 gm of sodium and 1600 ml of methanol. The mixture was stirred at 100° C for 3 hours, evaporated, the residue was introduced into water, and the aqueous mixture was extracted with ether. The 3-benzyl-11-hydroxy-1,2,4,5-tetrahydro-3H-azepino[4,5-b]quinoline formed at the same time remained undissolved.

Yield: 56.6% of theory; m.p.<20° C

EXAMPLE 208

11-Methoxy-1,2,4,5-tetrahydro-3-azepino[4,5-b]quinoline-carboxylic acid ethyl ester A mixture of 3.7 gm (11.6 millimols) of 3-benzyl-11-methoxy-1,2,4,5-tetrahydro-3H-azepino[4,5-b]quinoline, 1.1 ml (11.6millimols) of ethyl chloroformate and 35 ml of chloroform was stirred at 5° for 24 hours. After evaporation, the residue was chromatographed on silicagel with toluene/acetone (8:1) as the eluant.

Yield: 62% of theory; m.p. 122° C.

EXAMPLE 209

11-methoxy-1,2,4,5-tetrahydro-3H-azepino[4,5-b]quinoline was prepared from 11-methoxy-1,2,4,5-tetrahydro-3-azepino[4,5-b] quinoline-carboxylic acid ethyl ester by hydrolysis with semiconcentrated hydrochloric acid. Yield: 7% of theory; m.p. 112° C.

EXAMPLE 210

11-Methoxy-1,2,4,5-tetrahydro-3-azepino[4,5-b]quinoline-carboxylic acid ethyl ester-6-oxide was prepared from 11-methoxy -1,2,4,5-tetrahydro-3-azepino[4,5-b]quinoline-carboxylic acid ethyl ester and hydrogen peroxide analogous to Example 163. Yield: 15% of theory; m.p. 135° C.

EXAMPLE 211

3-Benzyl-11-[β-phenyl-ethyl]oxy-1,2,4,5-tetrahydro-3H-azepino [4,5-b]quinoline A mixture of 4.5 gm (15 millimols) of 3-benzyl-11-hydroxy-1,2,4,5-tetrahydro-3H-azepino[4,5-b]quinoline, 4.2 gm (30 millimols) of β-phenethyl chloride, 4.15 gm (30 millimols) of potassium carbonate, 5 gm of sodium iodide and 10 ml of butanone-(2) was boiled for 207 hours. The mixture was then suction-filtered, and the filter cake was purified by column chromatography on silicagel with ethyl acetate as the eluant. Yield: 73% of theory; m.p. <20° C.

EXAMPLE 212

11-[β-Phenyl-ethyl]oxy-1,2,4,5-tetrahydro-3-azepino[4,5-b] quinoline-carboxylic acid ethyl ester hydrochloride was prepared from 3-benzyl-11-[β-phenyl-ethyl]oxy-1,2,4,5-tetrahydro -3H-azepino[4,5-b]quinoline and ethyl chloroformate analogous to Example 208. Yield: 51% of theory; m.p. 153° C.

EXAMPLE 213

DL-3-Ethyl-11-[1-carbethoxyethyl-(1)]oxy-1,2,4,5-tetrahydro-3H-azepino[4,5-b]quinoline A mixture of 8 gm (25.4 millimols) of 3-ethyl-11-hydroxy-1,2,4,5-tetrahydro-3H-azepino[4,5-b]quinoline dihydrochloride, 8.3 gm (60 millimols) of potassium carbonate, 5.3 gm (30 millimols) of ethyl DL-α-bromopropionate, 5 gm of sodium iodide and 100 ml of butanone-(2) was boiled for 105 hours. The mixture was then evaporated, aqueous sodium bicarbonate solution was added, and the resulting mixture was extracted with ethyl acetate and evaporated. The evaporation residue was chromatographed on silicagel with chloroform/methanol (5:1) as the eluant. Yield: 22.4% of theory; m.p. 20° C.

EXAMPLE 214

DL-11-[1-Carbethoxyethyl-(1)]oxy-1,2,4,5tetrahydro-3-azepino [4,5-b]quinoline-carboxylic acid ethyl ester hydrochloride was prepared from 3-ethyl-11-[1-carbethoxyethyl-(1)]oxy-1,2,4,5-tetrahydro-3H-azepino[4,5-b]quinoline and ethyl chloroformate analogous to Example 208. Yield: 39.5% of theory; m.p. 133° C.

EXAMPLE 215

11-Chloro-1,2,4,5-tetrahydro-3-azepino[4,5-b]quinoline-carboxylic acid ethyl ester-6-oxide was prepared from 11-chloro-1,2,4,5-tetrahydro-3-azepino[4,5-b]quinoline-carboxylic acid ethyl ester and 30% hydrogen peroxide analogous to Example 163. Yield: 29% of theory; m.p. 170° C.

EXAMPLE 216

11-Hydroxy-2,3,4,5-tetrahydro-1H-2-azepino[4,3-b]quinoline-carboxylic acid ethyl ester was prepared from 2-benzyl-11-hydroxy-2,3,4,5-tetrahydro-1H-azepino[4,3-b]quinoline and ethyl chloroformate analogous to Example 208. Yield: 9% of theory; m.p. 285° C.

EXAMPLE 217

1,2,4,5-Tetrahydro-11-methyl-3-propyl-3H-azepino[4,5-b]quinoline, 2,3,4,5-tetrahydro-11-methyl-2-propyl-1H-azepino[4,3-b]quinoline and their dihydrochlorides by method A A mixture of 1.35 gm (7.1 millimols) of p-toluenesulfonic acid and 20 ml of toluene was boiled for 15 hours in a vessel equipped with a water trap. After addition of 0.96 gm (7.1 millimols) of 2-amino-acetophenone and 1.3 gm (7.1 millimols) of 4-ethoxy-2,3,6,7-tetrahydro-1-propyl-azepine, the mixture was boiled for 4 hours more in the vessel equipped with a water trap. After distilling off the toluene, the residue was dissolved in 2 N sodium hydroxide, and the solution was extracted with chloroform. The isomers of the bases thus obtained were separated by column chromatography on silicagel with methanol as the eluant and converted into the dihydrochlorides with isopropanolic hydrochloric acid. Yield of the dihydrochloride of the [4,5-b]-isomer: 5% of theory; m.p. 246° C. Yield of the dihydrochloride of the [4,3-b]-isomer: 21% of theory; m.p. 282° C.

EXAMPLE 218

1,2,4,5-Tetrahydro-11-methyl-3-propyl-3H-azepino[4,5-b]quinoline, 2,3,4,5-tetrahydro-11-methyl-2-propyl-1H-azepino[4,3-b]quinoline and their dihydrochlorides were prepared from 4-ethoxy-1,2,6,7-tetrahydro-1-propyl-5H-azepine and 2amino-acetophenone analogous to Example 217. Yield of the dihydrochloride of the [4,5-b]-isomer: 15% of theory; m.p. 245-246° C. Yield of the dihydrochloride of the [4,3-b]-isomer: 10% of theory; m.p. 282° C.

EXAMPLE 219

1,2,4,5-Tetrahydro-11-methyl-3-propyl-3H-azepino[4,5-b]quinoline, 2,3,4,5-tetrahydro-11-methyl-2-propyl-1H-azepino[4,3-b]quinoline and their dihydrochlorides by method A A mixture of 2 gm (8.7 millimols) of 1-propyl-hexahydro-azepinone-4-diethylketal and 1.18 gm (8.7 millimols) of 2-amino-acetophenone was heated at 140° C for 2 hours. After cooling, the mixture was suspended in 2 N sodium hydroxide, and the suspension was extracted with chloroform. The separation of the isomers was effected analogous to Example 217, and the pure isomers were converted into the dihydrochlorides with isopropanolic hydrochloric acid. Yield of the dihydrochloride of the [4,5-b]-isomer: 16% of theory; m.p. 246° C. Yield of the dihydrochloride of the [4,3-b]-isomer: 14% of theory; m.p. 282° C.

EXAMPLE 220

1,2,4,5-Tetrahydro-11-methyl-3-azepino[4,5-b]quinoline-carboxylic acid ethyl ester, 2,3,4,5-tetrahydro-11-methyl-1H-2-azepino[4,3-b]quinoline-carboxylic acid ethyl ester and their hydrochlorides were prepared from an isomer mixture of 1-ethoxycarbonyl-4-ethoxy-2,3,6,7-tetrahydro-azepine and 1-ethoxycarbonyl-4-ethoxy-5H-1,2,6,7tetrahydro-azepine (ratio: 1:1) and 2-amino-acetophenone analogous to Example 217. Yield of the dihydrochloride of the [4,5-b]-isomer: 52% of theory; m.p. 247° C. Yield of the dihydrochloride of the [4,3-b]-isomer: 43% of theory; m.p. 219° C.

EXAMPLE 221

1,2,4,5-Tetrahydro-11-methyl-3-azepino[4,5-b]quinoline-carboxylic acid ethyl ester, 2,3,4,5-tetrahydro-11-methyl-1H-2-azepino[4,3-b]quinoline-carboxylic acid ethyl ester and their hydrochlorides were prepared from 1-ethoxy-carbonyl-hexahydro-azepinone-(4)-diethylketal and 2-amino-acetophenone analogous to Example 219. Yield of the dihydrochloride of the [4,5-b]-isomer: 18% of theory; m.p. 247° C. Yield of the dihydrochloride of the [4,3-b]-isomer: 17% of theory; m.p. 219° C.

EXAMPLE 222

8,11-Dimethyl-1,2,4,5-tetrahydro-3-azepino[4,5-b]quinoline-carboxylic acid ethyl ester was prepared from 8,11-dimethyl-1,2,4,5-tetrahydro-3H-azepino[4,5-b]quinoline and ethyl chloroformate analogous to Example 155. Yield: 79% of theory; m.p. 121° C.

EXAMPLE 223

1,2,4,5-Tetrahydro-11-methyl-7-trifluoromethyl-3H-azepino[4,5-b]quinoline and 2,3,4,5-tetrahydro-11-methyl-7-trifluoromethyl-1H-azepino[4,3-b]quinoline were prepared from 2-amino-3-trifluoromethylacetopheone and hexahydro-azepinone-(4) hydrochloride analogous to Example 128. Yield of the [4,5-b]-isomer: 28% of theory; m.p. 78° C. Yield of the [4,3-b]-isomer: 27% of theory; m.p. 94° C.

EXAMPLE 224

10-Hydroxy-1,2,4,5-tetrahydro-11-methyl-3H-azepino[4,5-b]quinoline dihydrochloride was prepared by hydrolysis of 10-hydroxy-1,2,4,5-tetrahydro-11-methyl-3-azepino[4,5-b]quinoline-carboxylic acid ethyl ester in concentrated hydrochloric acid. Yield: 72% of theory; m.p. >300° C.

EXAMPLE 225

8-Hydroxy-1,2,4,5-tetrahydro-11-methyl-3H-azepino[4,5-b]quinoline dihydrochloride was prepared by hydrolysis of 8-hydroxy-1,2,4,5-tetrahydro-11-methyl-3-azepino[4,5-b]quinoline-carboxylic acid ethyl ester in concentrated hydrochloric acid. Yield: 34% of theory; m.p. 245° C (decomp.).

EXAMPLE 226

1,2,4,5-Tetrahydro-11-methyl-7-trifluoromethyl-3-azepino[4,5-b]quinoline-carboxylic acid ethyl ester was prepared from 1,2,4,5-tetrahydro-11-methyl-7-trifluoromethyl-3H-azepino[4,5-b]quinoline and ethyl chloroformate analogous to Example 155. Yield: 92% of theory; m.p. 136° C.

EXAMPLE 227

3-Amidino-1,2,4,5-tetrahydro-11-methyl-3H-azepino[4,5-b]quinoline 5 gm (23.6 millimols) of 1,2,4,5-tetrahydro-11-methyl-3H-azepino[4,5-b]quinoline were dissolved in 2.7 ml of glacial acetic acid and 20 ml of ethanol, and the solution was stirred at room temperature with 1.12 gm (26.6 millimols) of cyanamide for 72 hours. Thereafter, the product which had crystallized out was dissolved in water and reprecipitated with sodium hydroxide. Yield: 0.6 gm, 10% of theory; m.p. 140° C.

EXAMPLE 228

3-Carbamoyl-1,2,4,5-tetrahydro-11-methyl-3H-azepino[4,5-b]quinoline 3.3 gm (11.6 millimols) of 1,2,4,5-tetrahydro-11-methyl-3H-azepino[4,5-b]quinoline were reacted with 0.04 gm (11.6 millimols) of potassium cyanate at room temperature in 50 ml of water. After 4 to 6 hours, the reaction product crystallized out. Yield: 1 gm (34% of theory); m.p. 215° C (decomp.).

EXAMPLE 229

3-Thiocarbamoyl-1,2,4,5-tetrahydro-11-methyl-3H-azepino[4,5-b]quinoline was prepared by hydrolysis of 3-(benzamido-thiocarbonyl)-1,2,4,5-tetrahydro-11-methyl-azepino[4,5-b]quinoline (m.p. 175° C) in 2 N sodium hydroxide at room temperature. Yield: 36 % of theory; m.p. 218° C.

The compounds of the present invention, that is, those embraced by formula I, their 6-N-oxides, and non-toxic, pharmacologically acceptable acid addition salt thereof, have useful pharmacodynamic properties; more particularly, they exhibit primarily anorectic activities in warm-blooded animals, such as rats, as well as hypolipidemic, hypoglycemic, antidepressant, antiallergic and antiasthmatic activities. Especially noteworthy is the fact that the compounds of this invention have only a very minor effect upon the motility of the animals and produce very little or no cardiovascular effects.

The compounds of this invention were tested for anorectic activity, effect on motility and acute toxicity by the methods set forth below, and the results of these tests for a few representative species are shown in the tables, where A = 3-Ethyl-1,2,4,5-tetrahydro-11-methyl-3H-azepino[4,5-b]quinoline dihydrochloride,
B = 2,3,4,5-Tetrahydro-11-methyl-1H-azepino[4,3-b]quinoline dihydrochloride,
C = 1,2,4,5-Tetrahydro-11-methyl-3H-azepino[4,5-b]quinoline dihydrochloride,
D = 1,2,4,5-Tetrahydro-11-methyl-3-azepino[4,5-b]quinoline-carboxylic acid ethyl ester,
E = 1,2,4,5-Tetrahydro-11-propyl-3H-azepino[4,5-b]quinoline dihydrochloride,
F = 9-Chloro-1,2,4,5-tetrahydro-11-methyl-3H-azepino[4,5-b]quinoline dihydrochloride,
G = 1,2,4,5-Tetrahydro-11-methyl-3H-azepino[4,5-b]quinoline-6-N-oxide hydrochloride,
H = 5-Hydroxy-1,2,4,5-tetrahydro-11-methyl-3H-azepino[4,5-b]quinoline dihydrochloride,
I = 1,2,4,5-Tetrahydro-11-methyl-3propyl-3H-azepino[4,5-b]quinoline dihydrochloride,
J = 1,2,4,5-Tetrahydro-11-methyl-3azepino[4,5-b]quinoline-carboxylic acid tert.butyl ester hydrochloride,
K = 10-Chloro-1,2,4,5-tetrahydro-11-methyl-3H-azepino[4,5-b]quinoline dihydrochloide,
L = 5-Hydroxy-1,2,4,5-tetrahydro-11-methyl-3-azepino[4,5-b]quinoline-carboxylic acid ethyl ester,
M =3-(2-Hydroxy-propyl)-1,2,4,5-tetrahydro-11-methyl-3H-azepino[4,5-b]quinoline dihydrochloride and
N = 1,2,4,5-tetrahydro-11-methyl-3-azepino[4,5-b]quinoline-carboxylic acid methyl ester.

1. Effect on Intake of Food and Motility

Test animals:

Male albino rats with starting weights from 200 to 250 gm, kept in so-called makrolon-cages, three to a cage, in an air-conditioned room at a temperature of 22 ± 1° C and about 50 % relative humidity. Between test runs, food (standard feed Altromin R) and drinking water were freely accessible.

Test equipment:

A combination metabolism and motility test cage, described by J. M. van ROSSUM and F. SIMONS (Psychopharmacologia 14, 248, 1969) was used. With the aid of this device it is possible to measure the food intake and motoric activity on the same test animal.

Anorectic test:

For effecting and evaluating this test, a modified version of the method of J. SPENGLER and P. WASER [Arch. exp. Path. Pharmcol. 237, 171 (1959)] was used. A test group consisting of 6 ats was used for the test over a 3months' period, once a week, always on the same day of the week and at the same time of day. In preparation for the test, the animals were fasted for 24 hours while they had free access to drinking water. Then, they were put singly into the above-mentioned test cage for 2 hours, where a preweighed quantity of feed (Altromin-R, pulverized) and drinking water was offered ad libitum. Scattered feed was collected carefully, the consumed quantity of feed was determined by weighing the remaining quantity, and the food intake was calculated in terms of grams per 100 gm body weight. the test compound was injected subcutaneously or administered orally by esophageal sound at the beginning of the test period. Control tests showed that the variations of food consumption within a group on various days were lower than that between the various groups on the same day. Therefore, each group served as its own control. In the control tests the rats were given at the beginning of the 2 hour test period, 0.1 ml/100 gm water orally or 0.1 ml/100 gm physiological NaCl-solution subcutaneously. Before the test runs, 3 to 4 control tests were made and repeated later at intervals of 5 weeks. The average amount of the food intake which the animals had shown in the control tests was taken as the reference value. The anorectic activity of the test compound was expressed in terms of the percentage reduction of this reference value, and the median anorectic dose ($ED_{50}$), i.e. the dose which reduced the food intake by 50% over the reference value was graphically calculated.

Motility test:

The above-mentioned test cages were equipped with 3 light beams and corresponding photoelectric cells.

When the test animal moved about the cage, the light beams were interrupted, and the electric impulses generated thereby were registered by means of electronic counting devices.

The effect on motility was determined simultaneously with the above-described anorectic test and was evaluated in the same way. The control reference value was taken to be the average number of impulses registered over a period of 2 hours, during the control tests. The effect of the test compound was expressed in terms of percentage increase or decrease in the number of impulses produced by the treated animals over the control reference value, and the change in motility at the median anorectic dosage level was again graphically calculated.

The following table shows the results obtained from these tests.

| Compound | Anorectic $ED_{50}$ mgm/kg s.c. | % Change in Motility at anoretic $ED_{50}$ |
|---|---|---|
| A | 1.9 | + 7 |
| B | 1.1 | + 3 |
| C | 0.2 | − 23 |
| D | 0.8 | − 17 |
| E | 0.9 | − 21 |
| F | 1.5 | + 22 |
| G | 0.8 | − 14 |
| H | 0.3 | + 15 |
| I | 0.9 | − 14 |
| J | 1.1 | − 3 |
| K | 1.3 | + 26 |
| L | 4.0 | + 22 |
| M | 2.0 | + 33 |
| N | 1.8 | + 5 |

2. Acute Toxicity:

Groups of 10 male mice of the NMRI-strain with body weights between 18 and 30 gm. The animals were put individually into cylindrical jars and received by subcutaneous injection under the dorsal skin gradually increasing doses from 0.1 to 0.2 ml/10 gm of body weight of the test compound. The limits for the test dosage range had previously been determined on individual mice. The symptoms of poisoning were recorded. After an observation period of 24 hours the dead animals were counted. The determination of the median lethal dose ($LD_{50}$) according to G. KARBER [Arch. exper. Path. Pharmak. 162, 480, (1931)] concluded the test.

The following table shows the toxicity data obtained from this test and also the therapeutic ratio in relation to the anorectic $ED_{50}$.

| Compound | $LD_{50}$ mgm/kg s.c. | Therapeutic ratio $LD_{50}/ED_{50}$ |
|---|---|---|
| A | 180 | 95 |
| B | 195 | 177 |
| C | 83 | 415 |
| D | 810 | 1013 |
| E | 148 | 164 |
| F | 215 | 143 |
| G | 315 | 394 |
| H | 126 | 420 |

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective anorectic dosage unit of the compounds according to the present invention is from 0.016 to 0.34 mgm/kg body weight, preferably from 0.016 to 0.084 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 230

Tablets

The table composition is compounded from the following ingredients:

| | |
|---|---|
| 1,2,4,5-Tetrahydro-11-methyl-3H-azepino[4,5-b]quinoline dihydrochloride | 5.0 parts |
| Lactose | 60.0 parts |
| Corn starch | 50.0 parts |
| Soluble starch | 4.5 parts |
| Magnesium stearate | 0.5 parts |
| Total | 120.0 parts |

Preparation:

The azepinoquinoline compound is admixed with the lactose and the corn starch, the mixture is uniformly moistened with an aqueous solution of the soluble starch, the moist mass is granulated by forcing it through a 1.5 mm-mesh screen, and the granulate is dried at 50° C in a drying chamber with circulating air and then again passed through a 1.0 mm-mesh screen. The dry granulate is intimately admixed with the magnesium stearate, and the composition is compressed into 120 mgm-tablets in a conventional tablet making machine. Each tablet contains 5 mgm of the azepinoquinoline compound and is an oral dosage unit composition with effective anorectic action.

EXAMPLE 231

Coated pills

The pill core composition is compounded from the following ingredients:

| | |
|---|---|
| 1,2,4,5-Tetrahydro-11-methyl-3-azepino[4,5-b]quinoline-carboxylic acid ethyl ester | 2.5 parts |
| Lactose | 40.0 parts |
| Corn starch | 34.2 parts |
| Soluble starch | 3.0 parts |
| Magnesium stearate | 0.3 parts |
| Total | 80.0 parts |

Preparation:

The pill core composition is compounded in the same manner as the tablet composition in the preceding example, and it is compressed into 80 mgm-pill cores which are subsequently coated with a thin shell consisting essentially of a mixture of talcum and sugar, and the coated pills are polished with beeswax. Each pill contains 2.5 mgm of the azepinoquinoline compounds and is an oral dosage unit composition with effective anorectic action.

EXAMPLE 232

Suppositories

The suppository composition is compounded from the following ingredients:

| | |
|---|---|
| 5-Hydroxy-1,2,4,5-tetrahydro-11-methyl-3-azepino[4,5-b]quinoline-carboxylic acid ethyl ester | 10.0 parts |
| Suppository base (e.g. cocoa butter) | 1690.0 parts |
| Total | 1700.0 parts |

Preparation:

The suppository base is melted and cooled to 38° C, the azepinoquinoline compound is homogeneously blended into the molten mass, and 1700 mgm-portions of the composition are poured into cooled suppository molds and allowed to harden therein. Each suppository contains 10 mgm of the azepinoquinoline compound and is a rectal dosage unit composition with effective anorectic action.

EXAMPLE 233

Solution

The solution is compounded from the following ingredients:

| | |
|---|---|
| 3-Allyl-1,2,4,5-tetrahydro-11-methyl-3H-azepino[4,5-b]quinoline dihydrochloride | 0.04 parts |
| Carboxymethyl cellulose | 0.1 parts |
| Methyl p-hydroxy-benzoate | 0.05 parts |
| Propyl p-hydroxy-benzoate | 0.01 parts |
| Cane sugar | 10.0 parts |
| Glycerin | 5.0 parts |
| Sorbitol solution, 70 % | 20.0 parts |
| Flavoring | 0.3 parts |
| Distilled water q.s.ad | 100.0 parts by vol. |

Preparation:

The p-hydroxy-benzoates, the glycerin and the carboxymethyl cellulose are dissolved in the distilled water at 70° C; the solution is cooled to room temperature, and the azepinoquinoline compound is dissolved therein while stirring. Subsequently, the sugar, the sorbitol solution and the flavoring are stirred in, and the resulting solution is de-aerated by stirring in vacuo. 5 ml of the solution contain 2 mgm of the azepinoquinoline compound and are an oral dosage unit composition with effective anorectic action.

EXAMPLE 234

Coated sustained-release pills

The pill core composition is compounded from the following ingredients:

| | |
|---|---|
| 3-(β-Hydroxy-propyl)-1,2,4,5-tetrahydro-11-methyl-3H-azepino[4,5-b]quinoline | 10.0 parts |
| Carboxymethyl cellulose | 160.0 parts |
| Stearic acid | 10.0 parts |
| Polyvinyl acetate | 20.0 parts |
| Total | 200.0 parts |

Preparation:

The azepinoquinoline compound, the carboxymethyl cellulose and the stearic acid are intimately admixed with each other, the mixture is kneaded with a solution of the polyvinyl acetate in 100 ml of acetone, the resulting moist mass is forced through a 1.5 mm-mesh screen, and the granulate thus obtained is dried at 50° C in a drying chamber with circulating air and then again passed through the above screen. The resulting composition is compressed into 200 mgm-pill cores which are subsequently coated in conventional manner with a thin shell consisting essentially of a mixture of sugar and talcum and finally polished with beeswax. Each coated pill contains 10 mgm of the azepinoquinoline compound and is an oral dosage unit composition with effective anorectic action which releases the active ingredient over a period of about six hours.

Analogous results are obtained when any one of the other azepinoquinoline commpounds of this invention is substituted for the particular active ingredient in Examples 230 through 234. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

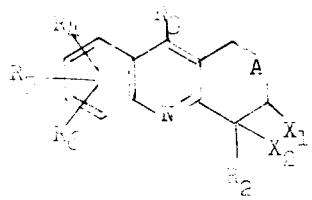

wherein

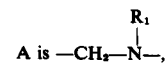

where
R₁ is hydrogen, carboxyl, of 2 to 7 carbon atoms, cyclohexyloxycarbonyl, benzyl, methylbenzyl, alkenyl of 2 to 6 carbon atoms, phenyl, trifluoroacetyl, amidino, aminocarbonyl or — B — X where
B is straight or branched alkylene of 1 to 6 carbon atoms, and
X is hydrogen, hydroxyl, methoxy, cyano or carbalkoxy of 2 to 6 carbon atoms,
R₂ is hydrogen, hydroxyl, alkyl of 1 to 3 carbon atoms, amino, dimethylamino or halogen,
R₃ is hydrogen, halogen, hydroxyl, straight or branched alkyl of 1 to 6 carbon atoms, cyclohexyl, alkoxy of 1 to 3 carbon atoms, phenylalkoxy of 1 to 3 carbon atoms, carbalkoxy of 2 to 4 carbon atoms-alkoxy of 1 to 3 carbon atoms, carbalkoxy of 2 to 4 carbon atoms, hydroxymethyl, phenyl, phenoxy, amino or pyrrolidino,
R₄, R₅ and R₆ are each hydrogen, halogen, methyl, hydroxyl, methoxy, amino or carbalkoxy of 2 to 4 carbon atoms, or any two of R₄, R₅ and R₆ together are 8,9-methylenedioxy, or any one of R₄, R₅ and R₆ is cyano, nitro or trifluoromethyl, and $X_1$ and $X_2$ are hydrogen or together form a double bond, a 6-N-oxide thereof, or a non-toxic, pharmacologically acceptable acid addition salt thereof.

2. A compound of claim 1, wherein

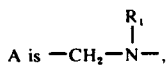

where
$R_1$ is hydrogen, alkyl of 1 to 3 carbon atoms, hydroxy-alkyl of 1 to 3 carbon atoms, carbalkoxy of 2 to 5 carbon atoms, allyl or amidino,
$R_2$ is hydrogen, methyl or hydroxyl,
$R_3$ is hydrogen, halogen or alkyl of 1 to 3 carbon atoms,
$R_4$, $R_5$ and $R_6$ are each hydrogen, chlorine, bromine, methyl, hydroxyl, methoxy or amino, or any one of $R_4$, $R_5$ and $R_6$ is trifluoromethyl or nitro, and
$X_1$ and $X_2$ are hydrogen,
a 6-N-oxide thereof, or a non-toxic, pharmacologically acceptable acid addition salt thereof.

3. A compound of claim 2, which is 3-($\beta$-hydroxypropyl)-1,2,4,5-tetrahydro-11-methyl-3H-azepino[4,5-b]-quinoline or a non-toxic, pharmacologically acceptable acid addition salt thereof.

4. A compound of claim 2, which is 1,2,4,5-tetrahydro-11-methyl-3-n-propyl-3H-azepino[4,5-b]quinoline or a non-toxic, pharmacologically acceptable acid addition salt thereof.

5. A compound of claim 2, which is 3-allyl-1,2,4,5-tetrahydro-11-methyl-3H-azepino[4,5-b]quinoline or a non-toxic, pharmacologically acceptable acid addition salt thereof.

6. A compound of claim 2, which is 1,2,4,5-tetrahydro-11-methyl-3-azepino[4,5-b]quinoline-carboxylic acid ethyl ester or a non-toxic, pharmacologically acceptable acid addition salt thereof.

7. A compound of claim 2, which is 1,2,4,5-tetrahydro-11-methyl-3-azepino[4,5-b]quinoline-carboxylic acid tert. butyl ester or a non-toxic, pharmacologically acceptable acid addition salt thereof.

8. A compound of claim 2, which is 5-hydroxy-1,2,4,5-tetrahydro-11-methyl-3-azepino[4,5-b]quinoline-carboxylic acid ethyl ester or a non-toxic, pharmacologically acceptable acid addition salt thereof.

9. A compound of claim 2, which is 1,2,4,5 - tetrahydro-11 - methyl - 3 - azepino[4,5 - b]quinoline - carboxylic acid methyl ester or a non-toxic, pharmacologically acceptable acid addition salt thereof.

* * * * *

PO-1050
(5/69)

UNITED STATES PATENT OFFICE
CERTIFICATE OF CORRECTION

Patent No. 3,987,047      Dated October 19, 1976

Inventor(s) GERHART GRISS, RUDOLF HURNAUS, WOLFGANG GRELL, ROBERT SAUTER and RICHARD REICHL It is certified that error appears in the above-identified patent and that said Letters Patent are hereby corrected as shown below:

Col. 7 line 9    "tetrahydro" should read -- Tetrahydro --

Col. 16 line 38    "he" should read -- the --

Col. 18 line 10    "he" should read -- the --

Col. 19 line 17    "-tetrohydro-" should read -- -tetrahydro- --

Col. 20 line 3    after "100" and before "of" -- ml -- should be inserted

Col. 24 line 19    "azeino" should read -- azepino --

Col. 52 line 46    after "carboxyl," -- carbalkoxy -- should be inserted

Signed and Sealed this

Fourth Day of January 1977

[SEAL]

Attest:

RUTH C. MASON  
*Attesting Officer*

C. MARSHALL DANN  
*Commissioner of Patents and Trademarks*